(12) United States Patent
Lafferty et al.

(10) Patent No.: US 6,972,183 B1
(45) Date of Patent: Dec. 6, 2005

(54) CAPILLARY ARRAY-BASED ENZYME SCREENING

(75) Inventors: William Michael Lafferty, Encinitas, CA (US); Jay M. Short, Encinitas, CA (US); Martin Keller, San Diego, CA (US)

(73) Assignee: Diversa Corporation, San Diego, CA (US)

( * ) Notice: Subject to any disclaimer, the term of this patent is extended or adjusted under 35 U.S.C. 154(b) by 0 days.

(21) Appl. No.: 09/444,112

(22) Filed: Nov. 22, 1999

Related U.S. Application Data

(63) Continuation-in-part of application No. 08/876,276, filed on Jun. 16, 1997.

(51) Int. Cl.$^7$ .......................................... G01N 33/573
(52) U.S. Cl. ........................... 435/7.4; 435/7.2; 435/6; 435/4; 435/DIG. 17; 435/DIG. 15; 435/DIG. 14; 536/23.2; 536/23.1
(58) Field of Search .................... 435/6, 91.1, 91.2, 435/183, 7.4, 7.2, 4; 536/23.1, 24.3, 24.33

(56) References Cited

U.S. PATENT DOCUMENTS

| | | | |
|---|---|---|---|
| 4,276,048 A | 6/1981 | Leaback | |
| 4,621,059 A | 11/1986 | Rokugawa | |
| 5,274,240 A | 12/1993 | Mathies et al. | |
| 5,584,982 A | 12/1996 | Dovichi et al. | |
| 5,670,113 A | 9/1997 | Akong et al. | |
| 5,675,155 A | 10/1997 | Pentoney, Jr. et al. | |
| 5,741,411 A | 4/1998 | Yeung et al. | |
| 5,763,263 A | 6/1998 | Dehlinger | |
| 5,790,727 A | 8/1998 | Dhadwal et al. | |
| 5,824,485 A * | 10/1998 | Thompson et al. ............ | 435/6 |
| 5,833,827 A | 11/1998 | Anazawa et al. | |
| 5,843,767 A | 12/1998 | Beattie | |
| 5,938,908 A | 8/1999 | Anazawa et al. | |
| 6,027,873 A | 2/2000 | Schellenberger et al. | |
| 6,048,444 A | 4/2000 | Takahashi et al. | |
| 6,054,032 A | 4/2000 | Haddad et al. | |
| 6,068,977 A * | 5/2000 | Perlin ............................ | 435/6 |
| 6,083,763 A | 7/2000 | Balch | |
| 6,086,740 A | 7/2000 | Kennedy | |
| 6,086,825 A | 7/2000 | Sundberg et al. | |
| 6,090,251 A | 7/2000 | Sundberg et al. | |
| 6,406,893 B1 * | 6/2002 | Knapp et al. .............. | 435/91.2 |

FOREIGN PATENT DOCUMENTS

| | | |
|---|---|---|
| WO | WO 90/14590 | 11/1990 |
| WO | WO 97 45730 A1 | 12/1997 |
| WO | WO 98/04920 | 2/1998 |
| WO | WO 98 28075 A1 | 7/1998 |
| WO | WO 98 38490 A1 | 9/1998 |
| WO | WO 99/34920 | 7/1999 |
| WO | WO 99 39191 A1 | 9/1999 |
| WO | WO 99 49294 A2 | 9/1999 |

OTHER PUBLICATIONS

Margolles–Clark, VTT Publications, (1996), 276, pages.*

* cited by examiner

*Primary Examiner*—T. D. Wessendorf

(57) ABSTRACT

A process for screening an expression library to identify clones expressing enzymes having a desired activity is provided. The process involves first generating from genomic DNA samples of one or more microorganisms an expression library comprising a plurality of recombinant cell clones, and then introducing into capillaries in a capillary array a substrate and at least a subset of the clones, either individually or as a mixture. Interaction of the substrate and a clone expressing an enzyme having the desired activity produces an optically detectable signal, which can then be spatially detected to identify capillaries containing clones producing such a signal. The signal-producing clones can then be recovered from the identified capillaries.

29 Claims, 10 Drawing Sheets

SEQUENCE LISTING

<160> NUMBER OF SEQ ID NOS: 2

<210> SEQ ID NO 1
<211> LENGTH: 20
<212> TYPE: DNA
<213> ORGANISM: Artificial sequence
<220> FEATURE:
<223> OTHER INFORMATION: Eubacterial forward primer

<400> SEQUENCE: 1
agagtttgat cctggctcag                                         20

<210> SEQ ID NO 2
<211> LENGTH: 19
<212> TYPE: DNA
<213> ORGANISM: Artificial sequence
<220> FEATURE:
<223> OTHER INFORMATION: Eubacterial reverse primer

<400> SEQUENCE: 2
ggttaccttg ttacgactt                                          19

CAPILLARY ARRAY-BASED ENZYME SCREENING

This application is a continuation-in-part of U.S. application Ser. No. 08/876,276, filed Jun. 16, 1997.

FIELD OF THE INVENTION

The present invention relates generally to the screening and identification of new enzymes and other bioactive molecules. More specifically, the present invention relates to methods, using optical detection and capillary array-based techniques, for screening expression libraries and recovering enzymes having a desired activity or the nucleic acid sequences encoding such enzymes.

BACKGROUND OF THE INVENTION

A need exists in the chemical industry for efficient catalysts, especially for use in the synthesis of optically pure materials. Enzymes can provide a solution to this need. The synthesis of polymers, pharmaceuticals and agrochemicals is often hampered by expensive processes that produce harmful byproducts and which suffer from low enantioselectivity (Faber, 1995; Faber, Tonkovich and Gerber, U.S. Dept. of Energy study, 1995). Enzymes possess a number of advantages that overcome these problems, including their ability to act on single functional groups, to distinguish between similar functional groups on a single molecule, and to distinguish between enantiomers. Moreover, enzymes are biodegradable and function at very low concentrations in reaction mixtures. Because of their chemo-, regio- and stereospecificity, enzymes present a unique opportunity to obtain selective transformations. Such transformations are often extremely difficult to duplicate chemically, especially in single-step reactions. The elimination of the need for protective groups and the ability to carry out multi-step transformations in a single reaction vessel, along with the concomitant reduction in environmental burden, has led to the increased demand for enzymes in the chemical and pharmaceutical industries (Faber, 1995). Enzyme-based processes have been gradually replacing many conventional chemical-based methods (Wrotnowski, 1997). However, a current limitation to more widespread industrial use of enzymes is the relatively small number of commercially available enzymes. Only approximately 300 enzymes (excluding DNA-modifying enzymes) are at present commercially available from the over 3000 non DNA-modifing enzymes thus far described in the literature.

The use of enzymes may also require in certain applications performance under demanding conditions, including activities in environments or on substrates for which the currently known arsenal of enzymes was not evolutionarily selected. Enzymes have evolved by selective pressure to perform very specific biological functions within the milieu of a living organism, under conditions of mild temperature, pH and salt concentration. For the most part, the non-DNA modifying enzymes thus far described (Enzyme Nomenclature, 1992) have been isolated from mesophilic organisms, which represent a very small fraction of the available phylogenetic diversity (Amann et al., 1995). The field of biocatalysis takes on a new dimension with the help of enzymes isolated from microorganisms that thrive in extreme environments. Such enzymes function at temperatures above 100° C. in terrestrial hot springs and deep sea thermal vents, at temperatures below 0° C. in arctic waters, in the saturated salt environment of the Dead Sea, at pH values around 0 in coal deposits and geothermal sulfur-rich springs, or at pH values greater than 11 in sewage sludge (Adams and Kelly, 1995). Enzymes obtained from these extremophilic organisms open a new field in biocatalysis. For example, several esterases and lipases cloned and expressed from extremophilic organisms are remarkably robust, showing high activity throughout a wide range of temperatures and pHs. This suggests that more diverse enzymes fulfilling the need for new biocatalysts can be found by screening biodiversity.

Virtually all presently known enzymes have come from cultured organisms (Enzyme Nomenclature, 1992). Traditional enzyme discovery programs rely solely on cultured microorganisms for their screening programs and, thus, only access a small fraction of natural diversity. Several recent studies have estimated that only a small percentage, conservatively less than 1%, of organisms present in the natural environment have been cultured (Amann et al., 1995; Barnes et al., 1994; Torvsik, 1990). For example, there have been recent reports of untapped diversity in water and sediment samples from the "Obsidian Pool" in Yellowstone National Park (Barnes, 1994). Amplification and cloning of 16S rRNA-encoding sequences revealed mostly unique sequences with little or no representation of the organisms which had previously been cultured from this pool, suggesting substantial diversity of archaea with so far unknown morphological, physiological and biochemical features. Similar studies on the cyanobacterial mat of Octopus Spring in Yellowstone Park have confirmed that tremendous uncultured diversity exists (Bateson et al., 1989). Giovannoni et al. (1990) reported similar results using bacterioplankton collected in the Sargasso Sea while Torvsik et al. (1990) have shown by DNA reassociation kinetics that there is considerable diversity in soil samples. Hence, this vast majority of microorganisms represents an untapped resource for the discovery of novel biocatalysts. In order to access this potential catalytic diversity, recombinant clone and enzyme screening approaches are required.

When attempting to identify a gene encoding a molecule having an activity of interest from a complex environmental expression library, rate-limiting steps occur at both the cloning level and the screening level. Screening of complex environmental libraries that contain, for example, hundreds of different organisms requires the analysis of up to several million clones. High-throughput screening methods are necessary to handle the enormous numbers of clones present in these libraries. Prior art methods, however, have various shortcomings that limit their usefulness in high-throughput screening of molecules or cells.

In a typical flow cytometer, individual cells pass through an illumination zone and appropriate detectors, gated electronically, measure the magnitude of a pulse representing the extent of light scattered. The magnitudes of these pulses are sorted electronically into "bins" or "channels", permitting the display of histograms of the number of cells possessing a certain quantitative property versus the channel number (Davey and Kell, 1996). Data accruing from flow cytometric measurements can be analyzed sufficiently rapidly that electronic cell-sorting procedures can be used to sort cells with desired properties into separate "buckets", a procedure usually known as fluorescence-activated cell sorting or FACS (Davey and Kell, 1996). The FACS method utilizes various fluorescent cell markers.

Enzymes, and cells expressing enzymes, can be detected using various chromogenic, lumigenic and fluorogenic substrates specific to those enzymes. Enzymes (or the cells expressing them), when contacted with chromogenic, lumigenic or fluorogenic substrates yield colored, luminescent and fluorescent products, respectively. Chromogenic substrates, such as ONPG (o-nitrophenyl-β-D-galactopyranoside), have been used to measure expression of β-galactosidase (β-gal) in cell cultures. But, it is generally not possible using flow cytometry to monitor expression in individual cells or to analyze the heterogeneity of expression in cell populations using chromogenic substrates. In contrast, the use of fluorogenic substrates makes it possible to determine β-gal activity in a large number of individual cells by means of flow cytometry. For example, in 1994, Plovins et al. reported the use of fluorescein-di-β-D-galactopyranoside (FDG) and 5-dodecanoylamino fluorescein di-β-D-galactopyranoside ($C_{12}$-FDG) as substrates for β-gal detection in animal, bacterial, and yeast cells.

There are currently no reports in the literature of screening, identification and recovery of recombinant clones or enzymes from environmental expression libraries using capillary array-based techniques. The present invention provides methods to allow the extremely rapid screening of recombinant clones to identify and recover enzymes having desirable activities, and the nucleic acids encoding such enzymes.

Capillary arrays have been used in a variety of applications, including assays, combinatorial library generation, DNA sequencing and electrophoresis. For example, U.S. Pat. No. 5,675,155 (to Pentoney, Jr., et al.) discloses a multicapillary fluorescent detection system for scanning a plurality of sample volumes confined within capillaries and detecting electromagnetic radiation (e.g., fluorescence emission) from the sample volumes. U.S. Pat. No. 5,763,263 (to Dehlinger) discloses methods of using capillary arrays to produce combinatorial position-addressable libraries through parallel chemical step-wise synthesis. U.S. Pat. No. 5,560,822 (to Briggs et al.) discloses multiplexed electrophoretic analysis methods using capillary arrays for-various applications including DNA sequencing.

SUMMARY OF THE INVENTION

In preferred embodiments, the present invention combines optical detection techniques with capillary arrays to provide methods for the high-throughput screening of recombinant expression clones. In the present invention, expression libraries derived from DNA, primarily DNA directly isolated from the environment, are screened very rapidly for activities of interest (e.g., binding or catalysis) utilizing optical (e.g., absorbance or fluorescence) detection of cells partitioned into capillary tubes in a capillary array. These libraries can contain greater than $10^8$ members and can represent single organisms or can represent the genomes of many (e.g., over 100) different microorganisms, species or subspecies.

One aspect of the present invention is a method for screening an expression library to identify a clone expressing, for example, an enzyme having a desired enzyme activity. This method involves, in one preferred embodiment, first generating (e.g., from genomic DNA samples of one or more microorganisms) an expression library comprising a plurality of recombinant clones, wherein the recombinant clones comprise host cells transformed with constructs comprising nucleic acid sequences derived from the DNA samples. A substrate and at least a subset of the clones is then introduced, either individually or together as a mixture, into capillaries in a capillary array. Interaction of the substrate and a clone expressing an enzyme having the desired enzyme activity produces an optically detectable signal, which can be spatially detected to identify one or more capillaries containing at feast one clone producing the signal. The signal-producing clones can then be recovered from the identified capillaries.

In a preferred embodiment, the expression library is multispecific, representing DNA from a plurality of microorganisms. Preferably also, the substrate and the subset of clones are introduced simultaneously as a mixture into capillaries in the capillary array by placing open ends of the capillaries (i.e., an open side of the capillary array) in a reservoir containing the mixture of substrate and clones.

Preferably, the clone identified by the foregoing method expresses an enzyme selected from the group consisting of: hydrolases, including epoxide hydrolases; hydratases, such as nitrile hydratases; nitrilases; lipases; esterases; proteases; peptidases; amidases; acylases; transaminases; phosphatases; glycosidases; reductases, including oxidoreductases; lyases; ligases; isomerases; polymerases; synthases; synthetases; transferases, such as glycosyl transferases; kinases; mono- and dioxygenases; peroxidases, including haloperoxidases, lignin peroxidases and diarylpropane peroxidases.

The microorganisms preferably comprise prokaryotic cells derived from an environmental sample. Preferred microorganisms for use in the present invention are selected from the group consisting of terrestrial microorganisms, marine microorganisms and airborne microorganisms. Especially preferred microorganisms are the extremophiles, particularly thermophiles. Other extremophiles include, but are not limited to, hyperthermophiles, psychrophiles, halophiles, psychrotrophs, alkalophiles, and acidophiles.

The host cell may be selected from the group consisting of bacterial cells, fungal cells, plant cells, insect cells and animal cells. The host cell can be a eukaryotic cell. Preferably, however, the host cell is a prokaryotic cell, such as a bacterial cell. A particularly preferred bacterial cell is *E. coli*.

The substrate is bioactive and produces a detectable optical signal upon interaction with an enzyme having the desired enzyme activity, or a clone expressing such enzyme. Preferably, the substrate is a fluorogenic substrate, such that the signal is optical fluorescence (including fluorescence polarization, time-resolved fluorescence and fluorescence resonance energy transfer, or FRET). Particularly preferred fluorogenic substrates include umbelliferone, fluorescein and. resorufin, as well as derivatives and analogues thereof. Alternatively, the substrate is a chromogenic substrate, such that the signal is optical absorbance (or a change therein), which can be calorimetrically detected.

Another aspect of the present invention is a method of identifying an enzyme having a desired enzyme activity, further comprising the step of isolating one or more enzymes from the clones recovered by the foregoing method.

Yet another aspect of the present invention is a method for screening an expression library to identify a nucleic acid sequence encoding an enzyme having a desired enzyme activity. This method involves, for example, first generating (e.g., from genomic DNA samples of one or more microorganisms) an expression library comprising a plurality of recombinant clones, wherein the recombinant clones comprise host cells transformed with constructs comprising nucleic acid sequences derived from the DNA samples. A substrate and at least a subset of the clones is then introduced, either individually or together as a mixture, into capillaries in a capillary array. Interaction of the substrate and a clone expressing an enzyme or protein having the desired enzyme or binding activity produces an optically detectable signal, which can be spatially detected to identify one or more capillaries containing at least one clone producing the signal. The signal-producing clones can then be recovered from the identified capillaries. A nucleic acid sequence encoding an enzyme having the desired enzyme activity can then be isolated from a signal-producing clone. This method may further include the step of sequencing the isolated nucleic acid sequence.

Another aspect of the present invention is a method of producing a recombinant enzyme having the desired enzyme activity. In this method, a nucleic acid sequence, which encodes an enzyme having a desired enzyme activity, is isolated according to the method described above. This sequence can then be inserted into a suitable expression vector to produce a transformable construct, which can be used to transform a suitable host cell to produce a recombinant cell. The recombinant enzyme expressed by the recombinant cell can then be recovered.

A further aspect is a method for identifying a mutant enzyme having a desired enzyme activity, further comprising subjecting an isolated enzyme to directed evolution. The directed evolution includes the steps of subjecting the enzyme to non-directed mutagenesis, and screening mutant enzymes produced thereby for a mutant enzyme having the desired enzyme activity.

The phrase "at least a subset of" refers to a whole unit or a portion thereof. In certain embodiments of the present invention, not all of the clones in a given expression library may be introduced into a capillary array. Thus, in the context of clones in an expression library, "at least a subset of" refers to all of the clones in the expression library, as well as any numerical fraction or portion thereof.

The term "spatial detection" refers to any technique or device capable of detecting a signal and attributing such signal to a given location or registry in a capillary array. Preferably, the spatial resolution of such detector is approximately equal to or better than the cross-sectional area of a single capillary.

Although the preferred embodiments involve the identification of enzymes and biocatalysts having a desired enzyme activity, the present invention is also useful for the screening, identification and recovery of other biomolecules having a desired biological activity. In particular, the capillary array-based techniques described herein can be used to identify proteins or ligands having a desired bioactivity or binding affinity. For example, binding assays may be conducted by using an appropriate substrate or other marker that emits a detectable signal upon the occurrence of the desired binding event. Many of the substrates discussed below, as well as numerous markers known in the art, are suitable for such binding assays.

The foregoing aspects, as well as attendant advantages, of the present invention will become apparent to one skilled in the art in view of the following detailed description and figures. The detailed description and figures illustrate certain preferred embodiments and are not intended to limit the scope of the invention, which is instead defined by the claims appended hereto and their legal equivalents.

BRIEF DESCRIPTION OF THE DRAWINGS

FIG. 9A illustrates a "sloppy" recovery in which the recovery device has an outer diameter greater than the inner diameter of the capillary from which one or more signal-producing clones is being recovered. FIG. 9B illustrates "precise" recovery in a preferred embodiment, in which the recovery device has an outer diameter approximately equal to or less than the inner diameter of the capillary.

DETAILED DESCRIPTION OF PREFERRED EMBODIMENTS

Figure 1:
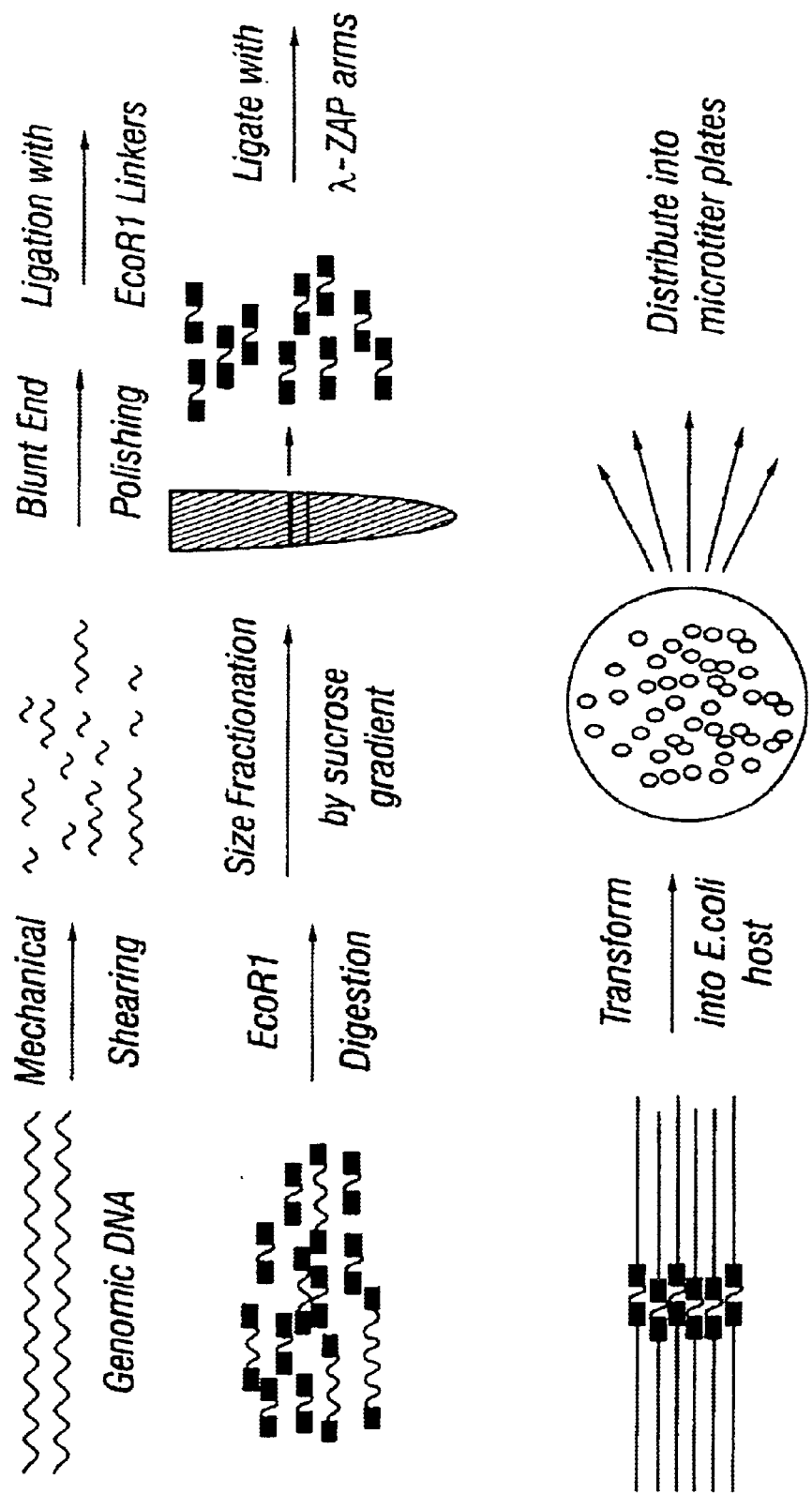
FIG. 1 illustrates the cloning of DNA fragments prepared by random cleavage of genomic DNA samples to generate an expression library in *E. coli* cells, as described in Example 1.

In the present invention, expression libraries generated from one or more microorganisms are screened for an activity of interest. Specifically, expression libraries are generated, clones are exposed to the substrate or substrate(s) of interest, and positive clones are identified and isolated. The present invention does not require cells to survive. The cells only need to be viable long enough to produce the compound to be detected, and can thereafter be either viable or non-viable cells, so long as the expressed biomolecule (e.g., enzyme) remains active.

In certain embodiments, the present invention provides an approach that combines direct cloning of genes encoding novel or desired bioactivities from environmental samples with an extremely high-throughput screening system designed for the rapid discovery of new molecules, such as enzymes. The approach is based on the construction of environmental "expression libraries" which can represent the collective genomes of numerous naturally occurring microorganisms archived in cloning vectors that can be propagated in *E. coli* or other suitable host cells. Because the cloned DNA can be initially extracted directly from environmental samples, the libraries are not limited to the small fraction of prokaryotes that can be grown in pure culture. Additionally, a normalization of the environmental DNA present in these samples could allow more equal representation of the DNA from all of the species present in a sample. Normalization techniques (described below) can dramatically increase the efficiency of finding interesting genes from minor constituents of the sample that may be underrepresented by several orders of magnitude compared to the dominant species.

The present invention permits the rapid screening of complex environmental expression libraries, representing, for example, thousands of different organisms. The analysis of a complex sample of this size requires one to screen up to several million clones to cover this genomic biodiversity. The present invention provides a high-throughput capillary array-based screening method that allows one to assess this enormous number of clones to identify and recover cells encoding useful enzymes, as well as other biomolecules (particularly ligands). While the preferred embodiments relate primarily to enzymes having a desired enzyme, activity, the present invention is also useful with regard to other biomolecules having a desired biological activity. In particular, the capillary array-based techniques described herein can be used to screen, identify and recover proteins having a desired bioactivity or other ligands having a desired binding affinity. For example, binding assays may be conducted by using an appropriate substrate or other marker that emits a detectable signal upon the occurrence of the desired binding event. Many of the substrates discussed below, as well as numerous markers known in the art, are suitable for such binding assays.

A. Generation of Expression Libraries

1. Microorganisms

The microorganisms from which the libraries may be prepared include prokaryotic microorganisms, such as Eubacteria and Archaebacteria, and lower eukaryotic microorganisms such as fungi, some algae and protozoa. Libraries may be produced directly from environmental samples, in which case DNA is recovered without culturing of an organism. Alternatively, the DNA may be recovered from a cultured organism, as described and exemplified in co-pending, commonly assigned U.S. Pat. No. 5,958,672, the disclosure of which is incorporated herein by reference. Such microorganisms include extremophiles, such as hyperthermophiles, psychrophiles, psychrotrophs, halophiles, alkalophiles, acidophiles, and the like. Sources of microorganism DNA include, for example, microbial samples obtained from Arctic and Antarctic ice, water or permafrost sources, materials of volcanic origin and materials from soil or plant sources in tropical areas. Preferred microorganisms for use in the present invention are selected from the group consisting of terrestrial microorganisms, marine microorganisms and airborne microorganisms.

The genomic DNA from such microorganisms may be employed to produce a recombinant expression library for subsequent determination of enzyme or other biological activity. Expression libraries generated using DNA from more than one species of microorganism are defined herein as multispecific expression libraries.

In one embodiment, cells isolated from the environment are, prior to the isolation of nucleic acid for generation of the expression library, sorted (e.g., by FACS) to separate prokaryotic cells based on, for example, DNA or AT/GC content of the cells. Various dyes or stains for FACS sorting are well known in the art. Other criteria can also be used to separate prokaryotic cells from the sample. DNA is then isolated from the cells and used for the generation of expression libraries.

Alternatively, the nucleic acid is isolated directly from the environment. DNA isolated directly from the environment, is used intact, randomly sheared or digested to general fragmented DNA. The DNA can then be bound to an intercalating agent and separated (e.g., by FACS) based on relative AT/GC base content to isolate DNA of interest. This sorted DNA can then be used for the generation of expression libraries.

2. Normalization

Normalization techniques are useful where there exists a variety of microorganism sources such as in consortia of microorganisms, primary enrichments, and environmental "uncultivated" samples. Normalization reduces the redundancy of clones from abundant species and increases the representation of clones from rare species. These normalized libraries allow for greater screening efficiency. Normalization techniques are described and exemplified in co-pending, commonly assigned pending U.S. application Ser. No. 08/665,565.

One embodiment for forming a normalized library from an environmental sample begins with the isolation of nucleic acid from the sample. The isolated nucleic acid can then be fractionated, and desired fractions can be recovered. DNA can be fractionated using a density centrifugation technique, such as a cesium-chloride gradient. When an intercalating agent, such as bis-benzimide is employed to change the buoyant density of the nucleic acid, gradients will fractionate the DNA based on relative base content. Nucleic acid from multiple organisms can be separated in this manner, and this technique can be used to fractionate complex mixtures of genomes. This can be of particular value when working with complex environmental samples.

Alternatively, the DNA does not have to be fractionated prior to normalization. Samples are recovered from the fractionated DNA, and the strands of nucleic acid are then melted and allowed to selectively reanneal under fixed conditions ($C_o t$ driven hybridization). When a mixture of nucleic acid fragments is melted and allowed to reanneal under stringent conditions, the common sequences find their complementary strands faster than the rare sequences. After an optional single-stranded nucleic acid isolation step, single-stranded nucleic acid representing an enrichment of rare sequences is amplified using techniques well known in the art, such as polymerase chain reaction or PCR (Barnes, 1994), and used to generate gene libraries.

3. DNA Isolation

DNA isolation is an important step in the generation of normalized or non-normalized DNA libraries from environmental samples composed of uncultivated organisms, or for the generation of such libraries from cultivated organisms. DNA can be isolated from samples using various techniques well known in the art (e.g., Nucleic Acids in the Environment Methods & Applications, J. T. Trevors and D. D. van Elsas, Springer Laboratory, 1995). Preferably, DNA thus isolated will be of large size and free of enzyme inhibitors or other contaminants. DNA can be isolated directly from an environmental sample (direct lysis), or cells may be harvested from the sample prior to DNA recovery (cell separation). Direct lysis procedures have several advantages over protocols based on cell separation. The direct lysis technique provides more DNA with a generally higher representation of the microbial community; however, it is sometimes smaller in size and more likely to contain enzyme inhibitors than DNA recovered using the cell separation technique. Direct lysis techniques have been described which provide DNA of high molecular weight and high purity (Barnes, 1994). If inhibitors are present, cell isolation protocols can be employed. Additionally, a fractionation technique, such as the bis-benzimide separation (cesium chloride isolation) described above, can be used to enhance the purity of the DNA.

Isolation of total genomic DNA from extreme environmental samples varies depending on the source and quantity of material. Uncontaminated, good quality (>20 kbp) DNA is preferred for the construction of a representative library. A successful general DNA isolation protocol is the standard cetyl-trimethyl-ammonium-bromide (CTAB) precipitation technique. In this technique, a biomass pellet is lysed and proteins digested by the nonspecific protease, proteinase K, in the presence of the detergent SDS. At elevated temperatures and high salt concentrations, CTAB forms insoluble complexes with denatured protein, polysaccharides and cell debris. Chloroform extractions are performed until the white interface containing the CTAB complexes is reduced substantially. The nucleic acids in the supernatant are precipitated with isopropanol and resuspended in TE buffer. For cells that are recalcitrant to lysis, a combination of chemical and mechanical methods with cocktails of various cell-lysing enzymes may be employed. Isolated nucleic acid may then further be purified using small cesium gradients.

4. Expression Vectors and Library Generation

An expression library can be generated by inserting the DNA isolated or derived from an environmental sample into a suitable expression vector which preferably contains expression regulatory sequences, such as promoters, enhancers and the like. Particularly preferred phage or plasmids, and methods for introduction and packaging into them, are described below.

An exemplary general procedure for producing libraries useful in the present invention is: obtaining Biomass DNA Isolation (various methods), shearing DNA (for example, with a 25-gauge needle), blunting DNA, methylating DNA, ligating to linkers, cutting back linkers, size-fractionating (for example, by a Sucrose Gradient), ligating to lambda expression vector, packaging (in vitro lambda packaging extract), plating on E. coli host and amplifying. This procedure is illustrated in FIG. 1.

As detailed in FIG. 1, cloning of DNA fragments prepared by random cleavage of the target DNA generates a representative library. DNA dissolved in TE buffer is vigorously passed through a 25-gauge double-hubbed needle until the sheared fragments are in the desired size range. The DNA ends are "polished" or blunted with Mung Bean Nuclease, and EcoRI restriction sites in the target DNA are protected with EcoRI Methylase. EcoRI linkers (GGAATTCC).are ligated to the blunted/protected DNA using a very high molar ratio of linkers to target DNA. This lowers the probability of two DNA molecules ligating together to create a chimeric clone. The linkers are cut back with EcoRI restriction endonuclease and the DNA is size-fractionated. The removal of sub-optimal DNA fragments and the small linkers is critical because ligation to the vector will result in recombinant molecules that are unpackageable, or the construction of a library containing only linkers as inserts. Sucrose gradient fractionation is used since it is extremely easy, rapid and reliable. Although the sucrose gradients do not provide the resolution of agarose gel isolations, they do produce DNA that is relatively free of inhibiting contaminants. The prepared target DNA is ligated to the lambda vector, packaged using in vitro packaging extracts and grown on the appropriate E. coli.

The DNA may be inserted into any of a variety of expression vectors using methods well known in the art. Such vectors include chromosomal, nonchromosomal and synthetic DNA sequences. Numerous suitable vectors are known to those of skill in the art, and are commercially available. Representative examples of expression vectors include viral particles, baculovirus, phage, plasmids, phagemids, cosmids, fosmids, bacterial artificial chromosomes, viral DNA (e.g. vaccinia, adenovirus, foul pox virus, pseudorabies and derivatives of SV40), P1-based artificial chromosomes, yeast plasmids, yeast artificial chromosomes, as well as other vectors specific for specific hosts of interest (such as bacillus, aspergillus, yeast, etc.) Specific examples of suitable vectors include—Bacterial: pQE vectors (Qiagen), pBluescript plasmids, pNH vectors, ZAP vectors (Stratagene), ptrc99a, pKK223-3, pDR540, pRIT2T (Pharmacia); Eukaryotic: pXTI, pSG5 (Stratagene), pSVK3, pBPV, pMSG, pSVLSV40 (Pharmacia). However, any other suitable vector may be used, so long as it is replicable and viable in the host.

A vector for use in the present invention preferably contains an f-factor origin replication. The f-factor (or fertility factor) in E. coli is a plasmid which effects high frequency transfer of itself during conjugation and less frequent transfer of the bacterial chromosome itself. A particularly preferred embodiment is to use cloning vectors, referred to as "fosmids" or bacterial artificial chromosome (BAC) vectors.

The DNA sequence in the expression vector is operatively linked to appropriate expression control sequencers) (promoter) to direct RNA synthesis. Specific bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is within the level of ordinary skill in the art. The expression vector preferably also contains a ribosome binding site for translation initiation and a transcription terminator. The vector may also include appropriate sequences for amplifying expression.

Generally, the vector will include replication origins and a promoter derived from a highly-expressed gene to direct transcription of a downstream structural sequence. Such promoters can be derived from operons encoding glycolytic enzymes, such as 3-phosphoglycerate kinase (PGK), acid phosphatase, or heat shock proteins, among others. The vector preferably contains one or more selectable marker genes to provide a phenotypic trait for selection of transformed host cells, such as dihydrofolate reductase or neomycin resistance for eukaryotic cell culture, and tetracycline or ampicillin resistance in E. coli.

The heterologous structural sequence is assembled in appropriate phase with translation initiation and termination sequences, and preferably, a leader sequence capable of directing secretion of translated protein into the periplasmic space or extracellular medium. The cloning strategy permits expression via both vector-driven and endogenous promoters; vector promotion may be important with expression of genes whose endogenous promoter will not function in E. coli.

Lambda vectors are preferred, because they can accommodate relatively large DNA sequences,.have high cloning and packaging efficiencies and are easy to handle and store compared to plasmid vectors. For example, λ-ZAP vectors (Stratagene Cloning Systems, Inc.) have a convenient subcloning feature that allows clones in the vector to be excised with helper phage into the pBluescript phagemid, eliminating the time involved in subcloning. The cloning site in these vectors lies downstream of the lac promoter. This feature allows expression of genes whose endogenous promoter does not function in E. coli.

5. Transformation of Host Cells

The constructs, comprising nucleic acid sequences derived from the genomic DNA samples of the microorganisms inserted into appropriate expression vectors, are introduced or transformed into a suitable host. The host cell may be selected from the group consisting of bacterial cells, fungal cells, plant cells, insect cells and animal cells. The host cell can be a eukaryotic cell. Preferably, however, the host cell is a prokaryotic cell, such as a bacterial cell. Particularly preferred host cells are E. coli.

Introduction of the construct into the host cell can be effected by any of a variety of methods known in the art including, for example, calcium phosphate transfection, DEAE-Dextran mediated transfection, or electroporation (Davis, L., Dibner, M., Battey, I., Basic Methods in Molecular Biology (1986)). The selection of an appropriate host is within the scope of those skilled in the art in view of the teachings herein. Host cells are genetically engineered (i.e., transduced or transformed or transfected) with the vectors. The engineered host cells can be cultured in conventional nutrient media modified as appropriate for activating promoters, selecting transformants or amplifying genes. The culture conditions, such as temperature, pH and the like, appropriate for use with a particular host cell are known or apparent to the ordinarily skilled artisan.

6. Biopanning

The expression libraries of the present invention may optionally be "biopanned." "Biopanning" refers to a process for identifying clones having a specified biological activity by screening for sequence homology in a library of clones prepared by: (i) selectively isolating target DNA derived from at least one microorganism by using at least one probe DNA comprising at least a portion of a DNA sequence encoding a molecule (e.g., an enzyme) having a specified biological (e.g., enzymatic) activity; and (ii) optionally, transforming a host with isolated target DNA to produce a library of clones which are screened for the specified biological activity. The probe DNA used for selectively isolating the target DNA can be a full-length coding region sequence or a partial coding region sequence for an enzyme of known activity. The probe DNA is preferably single-stranded and the microbial DNA that is probed has preferably been converted into single-stranded form. Particularly preferred probes are those derived from DNA-encoding enzymes having an activity similar or identical to the specified enzyme activity which is to be screened.

The probe DNA should be at least about 10 bases and, preferably, at least about 15 bases in length. Hybridization conditions are designed to provide a stringency of at least about 50% sequence identity; more preferably, a stringency of at least about 70% sequence identity is provided. The conditions used to achieve a particular level of stringency will vary depending on the nature of the nucleic acids being hybridized. For example, the length, degree of complementary, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter. The choice of appropriate hybridization is within the purview of the skilled artisan. An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

Hybridization techniques are well known in the art. Preferably, the probe DNA is "labeled" with one partner of a specific binding pair (i.e., a ligand) and the other partner of the pair is bound to a solid matrix to provide ease of separation of target DNA from its source. The ligand and specific binding partner can be selected from, in either orientation, the following: (1) an antigen or hapten and an antibody or specific binding fragment thereof; (2) biotin or iminobiotin and avidin or streptavidin; (3) a sugar and a lectin specific therefor, (4) an enzyme and an inhibitor therefor, (5) an apoenzyme and cofactor; (6) complementary homopolymeric oligonucleotides; and (7) a hormone and a receptor therefor. The solid phase is preferably selected from: (1) a glass or polymeric surface; (2) a packed column of polymeric beads; and (3) magnetic or paramagnetic particles.

Optionally, the isolated target DNA is amplified before being used to transform host cells. The double-stranded DNA selected to include as at least a portion thereof a predetermined DNA sequence can be rendered single-stranded, subjected to amplification and reannealed to provide amplified numbers of selected double-stranded DNA. Numerous amplification methodologies are well known in the art.

There are a number of permutations for performing the various steps of generating the expression library, biopanning, and screening the expression library. Examples include the following: (i) generating the library and then screening it; (ii) normalizing the DNA, generating the expression library and screening it; (iii) normalizing, generating the library, biopanning and screening; or (iv) generating, biopanning and screening the library.

B. Enzyme Screening

Having prepared an expression library comprising a multiplicity of clones comprising DNA selectively isolated from one or more organisms, the library is screened for a specific enzyme activity to identify and recover clones having the specified activity. The screening may be conducted on individual expression clones or on a mixture of expression clones. The clones that are identified as having the specified enzyme activity may then be sequenced to identify the DNA sequence encoding the enzyme having the specified activity. Thus, in accordance with the present invention, it is possible: (i) to isolate and identify DNA encoding an enzyme having a specified enzyme activity, (ii) to isolate and identify enzymes having such activity (including the amino acid sequence thereof) and (iii) to produce recombinant enzymes having such activity.

1. Enzyme Activities

The expression library may be screened for a variety of enzyme activities or binding relationships, including one or more of the six IUB classes: oxidoreductases, transferases, hydrolases, lyases, isomerases and ligases. The enzymes that are determined to be positive for one or more of the IUB classes may then be rescreened for a more specific enzyme activity. Alternatively, the library may be screened directly for a more specific enzyme activity. For example, the library may be screened for the type of bond on which the enzyme acts. Thus, for example, the library may be screened to ascertain those hydrolases which act on one or more specified chemical functionalities, such as: (a) amide or peptide bonds (e.g., proteases); (b) ester bonds, (e.g., esterases and lipases); and (c) acetals (e.g., glycosidases).

The present invention may be employed to identify new enzymes having, for example, the following enzymatic activities:

Lipase/Esterase. Enzymes having lipase or esterase activity are useful, for example, in enantioselective hydrolysis of esters (lipids)/thioesters, resolution of racemic mixtures, synthesis of optically active acids or alcohols from meso-diesters, selective syntheses, regiospecific hydrolysis of carbohydrate esters, selective hydrolysis of cyclic secondary alcohols, synthesis of optically active esters, lactones, acids, alcohols, transesterification of activated/nonactivated esters, interesterification, optically active lactones from hydroxyesters, regio- and enantioselective ring opening of anhydrides, detergents, fat/oil conversion, and cheese ripening.

Protease. Enzymes having protease activity are useful, for example, in ester/amide synthesis, peptide synthesis, resolution of racemic mixtures of amino acid esters, synthesis of non-natural amino acids, and detergents/protein hydrolysis.

Glycosidase/Glycosyl transferase. Enzymes having glycosidase or glycosyl transferase activity are useful, for example, in sugar/polymer synthesis, cleavage of glycosidic linkages to form mono, di-and oligosaccharides, synthesis of complex oligosaccharides, glycoside synthesis using UDP-galactosyl transferase, transglycosylation of disaccharides, glycosyl fluorides, aryl galactosides, glycosyl transfer in oligosaccharide synthesis, diastereoselective cleavage of α-glucosylsulfoxides, asymmetric glycosylations, food processing and paper processing.

Phosphatase/Kinase. Enzymes having phosphatase or kinase activity are useful, for example, in synthesis/hydrolysis of phosphate esters, regio- and enantioselective phosphorylation, introduction of phosphate esters, synthesis of phospholipid precursors, controlled polynucleotide synthesis, activation of biological molecules, and selective phosphate bond formation without protecting groups.

Mono-/Dioxygenase. Enzymes having mono- or dioxygenase activity are useful, for example, in direct oxyfunctionalization of unactivated organic substrates, hydroxylation of alkanes, aromatics, steroids, epoxidation of alkenes, enantioselective sulphoxidation, and regio- and stereoselective Bayer-Villiger oxidations.

Haloperoxidase. Enzymes having haloperoxidase activity are useful, for example, in oxidative addition of halide ion to nucleophilic sites, addition of hypohalous acids to olefinic bonds, ring cleavage of cyclopropanes, activated aromatic substrates converted to ortho and para derivatives, 1,3-diketones converted to 2-halo-derivatives, heteroatom oxidation of sulfur and nitrogen containing substrates, and oxidation of enol acetates, alkynes and activated aromatic rings.

Lignin peroxidase/Diarylpropane peroxidase. Enzymes having lignin peroxidase or diarylpropane peroxidase activity are useful, for example, in oxidative cleavage of C—C bonds, oxidation of benzylic alcohols to aldehydes, hydroxylation of benzylic carbons, phenol dimerization, hydroxylation of double bonds to form diols, and cleavage of lignin aldehydes.

Epoxide hydrolase. Enzymes having epoxide hydrolase activity are useful, for example, in synthesis of enantiomerically pure bioactive compounds, regio- and enantioselective hydrolysis of epoxides, resolution of racemic epoxides, and hydrolysis of steroid epoxides.

Nitrile hydratase/nitrilases. Enzymes having nitrile hydratase or nitrilase activity are useful, for example, in hydrolysis of aliphatic nitriles to carboxamides, hydrolysis of aromatic, heterocyclic, unsaturated aliphatic nitriles to corresponding acids, hydrolysis of acrylonitrile, production of aromatics and carboxamides, carboxylic acids (nicotinamide, picolinamide, isonicotinamide), regioselective hydrolysis of acrylic dinitrile and amino acids from hydroxynitriles Transaminase. Enzymes having transaminase activity are useful, for example, in transfer of amino groups into oxo-acids.

Amidase/Acylase. Enzymes having amidase or acylase activity are useful, for example, in hydrolysis of amides, amidines, and other C—N bonds, and non-natural amino acid resolution and synthesis.

Preferably, the present invention is used to identify and recover an enzyme selected from the group consisting of: hydrolases, including epoxide hydrolases; hydratases, such as nitrile hydratases; nitrilases; lipases; esterases; proteases; peptidases; amidases; acylases; transaminases; phosphatases; glycosidases; reductases, including oxidoreductases; lyases; ligases; isomerases; polymerases; synthases; synthetases; transferases, such as glycosyl transferases; kinases; mono- and dioxygenases; peroxidases, including haloperoxidases, lignin peroxidases and diarylpropane peroxidases.

2. Single Cell Screening Factors

Figure 2:
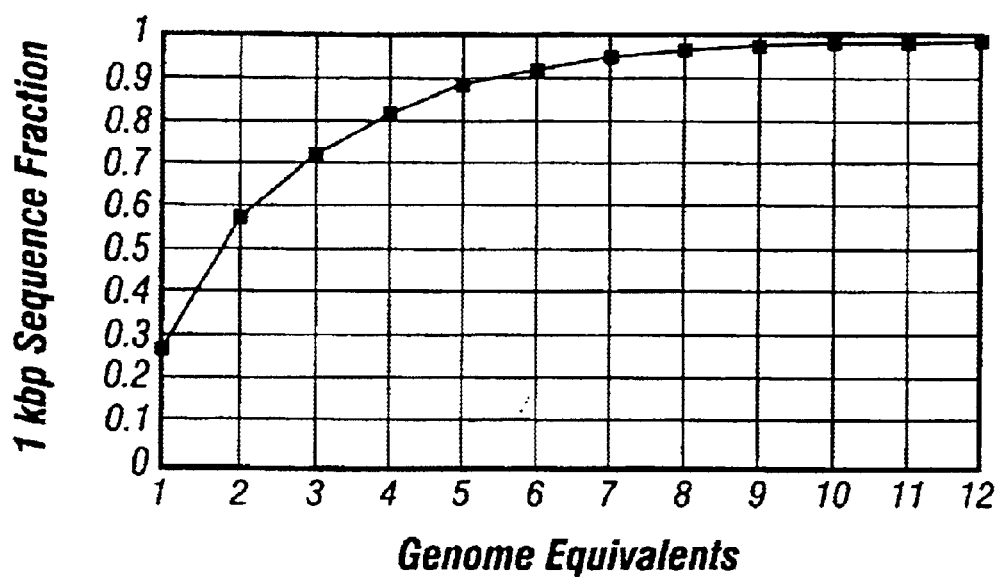
FIG. 2 shows a statistical analysis of the total number of clones to be tested (e.g., the number of genome equivalents). Assuming that mechanical shearing and gradient purification result in normal distribution of DNA fragment sizes with a mean of 4.5 kbp and a variance of 1 kbp, the fraction represented of all possible 1 kbp sequences in a 1.8 Mbp genome is plotted in FIG. 2 as a function of increasing genome equivalents.

There are two main factors that govern the screening of an enzyme in a single cell: (i) the level of gene expression; and (ii) the enzyme assay sensitivity. To estimate the level of gene expression, one can determine (given the vector) how many copies of the gene product will be produced by the host cell. For instance, one can assume that each *E. coli* cell infected with pBluescript phagemid (Stratagene Cloning Systems, Inc.) will produce ~$10^3$ copies of the gene product from the insert In order to assess the total number of clones to be tested (e.g., the number of genome equivalents), a statistical analysis can be performed. For example, assuming that mechanical shearing and gradient purification results in a normal distribution of DNA fragment sizes with a mean of 4.5 kbp and a variance of 1 kbp, the fraction represented of all possible 1 kbp sequences in a 1.8 Mbp genome is plotted in FIG. 2 as a function of increasing genome equivalents.

Based on these results, approximately 2,000 clones (5 genome equivalents) must be screened in order to achieve approximately 98% probability of obtaining a particular gene. Assuming that a complex environmental library contains about 1000 different organisms, at least 2,000,000 clones have to be screened to achieve an approximately 98% probability of obtaining a particular gene. This number rises dramatically assuming that the organisms differ vastly in abundance in natural populations.

3. Enzyme Substrates

Enzymes and substrates suitable for the optical detection of such enzymes (and their specific enzyme activities) are well known in the art. For example, various enzymes and suitable substrates specific for such enzymes are provided in *Molecular Probes: Handbook of Fluorescent Probes and*

*Research chemicals*(Molecular Probes, Inc.; Eugene, Oreg.), the disclosure of which is incorporated herein by reference. A suitable substrate for use in the present invention is any substrate that produces an optically detectable signal upon interaction (e.g., reaction) with a given enzyme having a desired activity, or a given clone encoding such enzyme.

One skilled in the art can choose a suitable substrate based on the desired enzyme activity. Examples of desired enzymes/enzyme activities include those listed above. A desired enzyme activity may also comprise a group of enzymes in an enzymatic pathway for which there exists an optical signal substrate. One example of this is the set of carotenoid synthesis enzymes.

Substrates are known and/or are commercially available for glycosidases, proteases, phosphatases, and monoxygenases, among others. Among the proteases with optical signal substrates are the serine proteases trypsin and chymotrypsin. Among the glycosidases are maimosidase, amyloglucosidase, cellulase, neuraminidase, β-galactosidase, β-glucosidase, β-glucuronidase, andα-amylase.

Where the desired activity is in the same class as that of other biomolecules or enzymes having a number of known substrates, the activity can be examined using a cocktail of the known substrates. For example, substrates are known for approximately 20 commercially available esterases and the combination of these known substrates can provide detectable, if not optimal, signal production.

The optical signal substrate can be a chromogenic substrate, a fluorogenic substrate, a bio- or chemi-luminescent substrate, or a fluorescence resonance energy transfer (FRET) substrate. The detectable species can be one which results from cleavage of the substrate or a secondary molecule which is so affected by the cleavage or other substrate/biomolecule interaction as to undergo a detectable change. Innumerable examples of detectable assay formats are known from the diagnostic arts which use immunoassay, chromogenic assay, and labeled probe methodologies.

In one embodiment, the optical signal substrate can be a bio- or chemi-luminescent substrate. Chemiluminescent substrates for several enzymes are available from Tropix (Bedford, Mass.). Among the enzymes having known chemiluminescent substrates are alkaline phosphatase, β-galactosidase, β-glucuronidase, and β-glucosidase.

In another embodiment, chromogenic substrates may be used, particularly for certain enzymes such as hydrolytic enzymes. For example, the optical signal substrate can be an indolyl derivative, which is enzymatically cleaved to yield a chromogenic product. Where chromogenic substrates are used, the optically detectable signal is optical absorbance (including changes in absorbance). In this embodiment, signal detection can be provided by an absorbance measurement using a spectrophotometer or the like.

In a preferred embodiment, fluorogenic substrates are used, such that the optically detectable signal is fluorescence. Fluorogenic substrates provide high sensitivity for improved detection, as well as alternate detection modes. Hydroxy- and amino-substituted coumarins are the most widely used fluorophores used for preparing fluorogenic substrates. A preferred coumarin-based fluorogenic substrate is 7-hydroxycoumarin, commonly known as umbelliferone (Umb). Derivatives and analogues of umbelliferone are also preferred. Substrates based on the derivatives and analogues of fluorescein (such as FDG or $C_{12}$-FDG) and rhodarnine are also preferred. Substrates derived from resorufm (e.g., resorufin β-D-galactopyranoside or resorufm β-D-glucuronide) are particularly preferred for use in the present invention. Resorufm-based substrates are useful, for example, in screening for glycosidases, hydrolases and dealkylases. Lipophilic derivatives of the foregoing substrates (e.g., alkylated derivatives) may be useful in certain embodiments, since they generally load more readily into cells and may tend to associate with lipid regions of the cell. Fluorescein and resorufin are available commercially as alkylated derivatives that form products that are relatively insoluble in water (i.e., lipophilic). For example, fluorescence imaging can be performed using $C_{12}$-resorufin galactoside, produced by Molecular Probes (Eugene, Oreg.) as a substrate.

Figure 3:
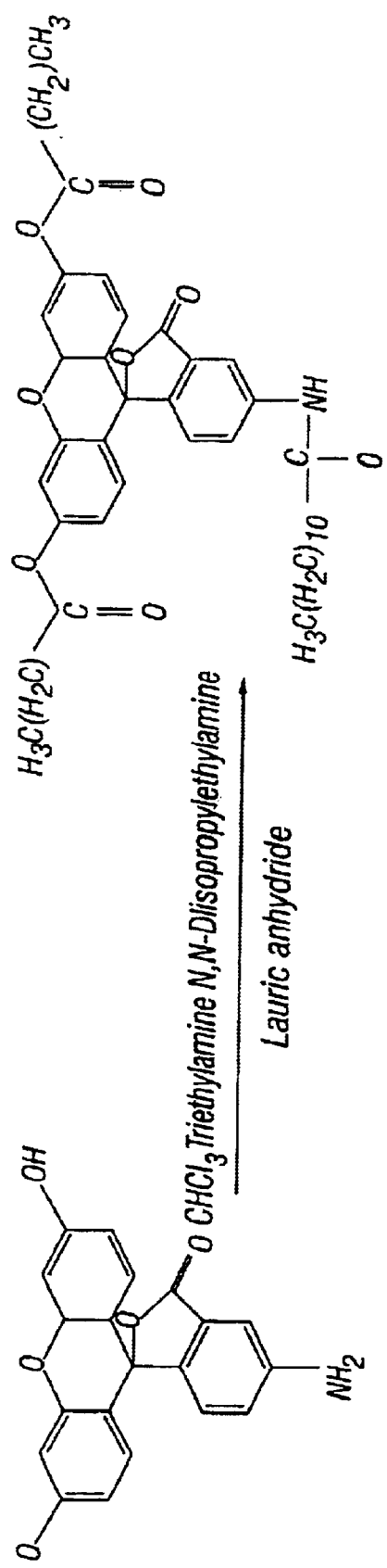
FIG. 3 shows the synthesis of 5-dodecanoly-aminofluorescein-di-dodecanoic acid ($C_{12}$-$FDC_{12}$), which can be used as a fluorogenic substrate for esterases and lipases.

The particular fluorogenic substrate used may be chosen based on the enzymatic activity being screened. For example:

Lipases/esterases. When screening for an enzyme having lipase or esterase activity, an acylated derivative of fluorescein is preferably used. The fluorophores is hydrolyzed from the derivative to generate a signal. Acylated derivatives of fluorescein can be synthesized according to the synthesis method illustrated in FIG. 3. In the reaction shown in FIG. 3, nine molar equivalents of lauric anhydride triethylamine and N,N-diisopropylethylamine are added to a solution of fluoresceinamine in chloroform. After the reaction is complete, the product 5, dodecanoyl-aminofluorescein-di-dodecanoic acid ($C_{12}$-$FDC_{12}$) is recrystallized.

Figure 4:
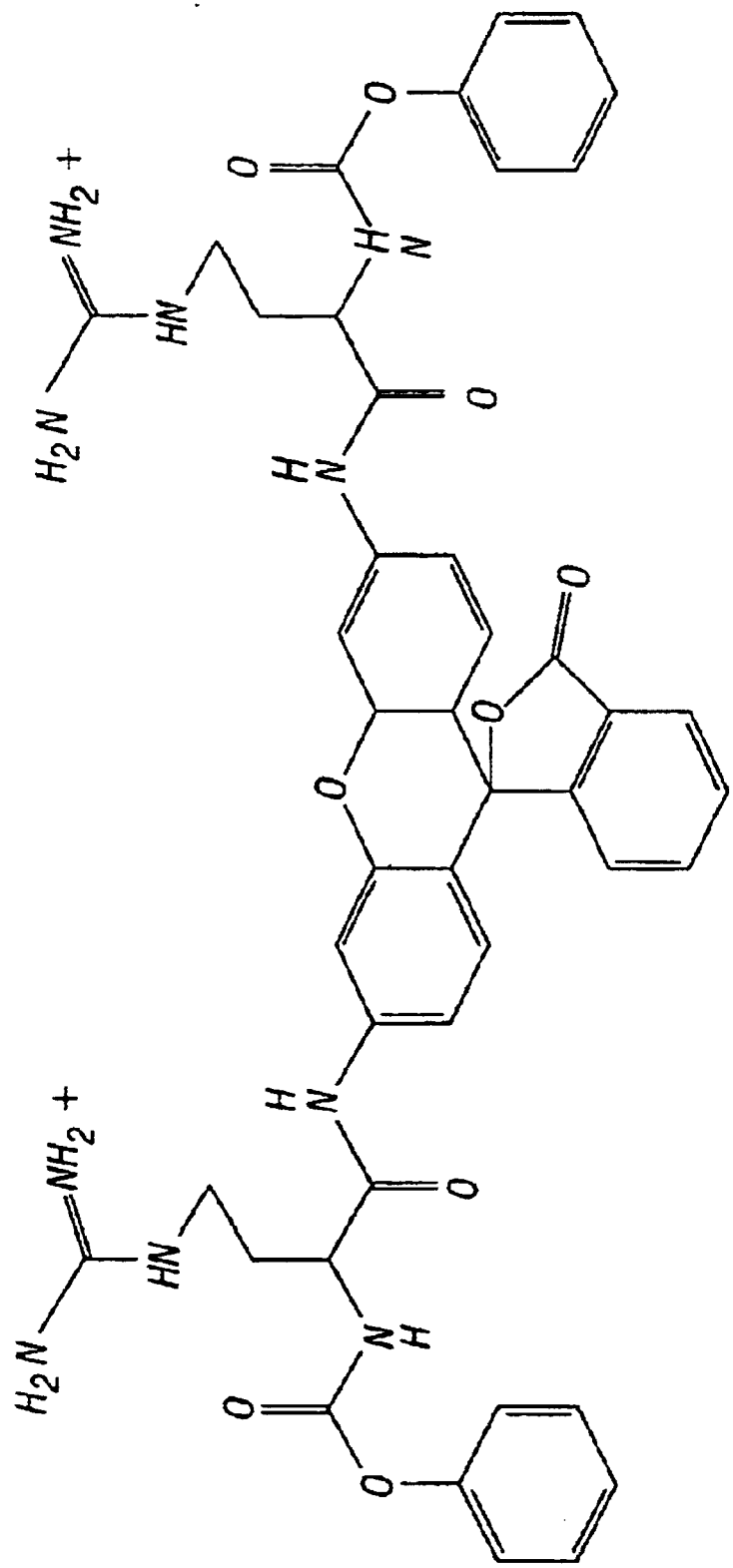
FIG. 4 shows the chemical structure of a rhodamine derivative useful as a fluorogenic substrate for proteases.
Figure 5:
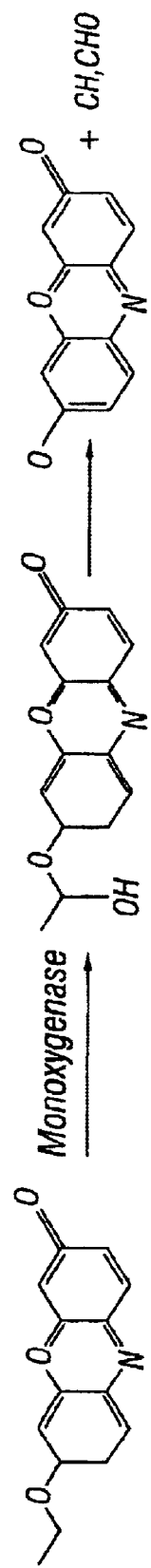
FIG. 5 shows a compound useful as a substrate for monooxygenases, which compound is converted into the resorufin fluorophore.

Proteases. Enzymes having protease activity can be screened in the same way as the esterases, with an amide being cleaved instead of an ester. There are now well over 100 different protease substrates available with an acylated fluorophore at the scissile bond. Rhodamine derivatives (see, e.g., FIG. 4) are generally preferred.

Monooxygenases (dealkylases). Compounds such as that depicted in FIG. 6 can be used as substrates for enzymes having monooxygenase activity. Hydroxylation of the ethyl group in the compound results in the release of the resorufin fluorophore. Several unmodified coumarin derivatives suitable as-monooxygenase substrates are commercially available.

Preferably, the substrate is able to enter the cell and maintain its presence within the cell for a period sufficient for analysis to occur (i.e., so that once the substrate is in the cell it will not "leak" back out before reacting with the enzyme being screened to an extent sufficient to produce a detectable response). Retention of the substrate in the cell can be enhanced by a variety of techniques. In one method, the substrate compound is structurally modified by addition of a hydrophobic (e.g., alkyl) tail. In another, certain preferred solvents, such as DMSO or glycerol, can be used to coat the exterior of the cell. Also, the substrate can be administered to the cells at reduced temperature, which has been observed to retard leakage of substrate from cells.

The optical signal substrate can, in certain embodiments, be a FRET substrate. FRET is a spectroscopic method that can monitor proximity and relative angular orientation of fluorophores. A fluorescent indicator system that uses FRET to measure the concentration of a substrate or products includes two fluorescent moieties having emission and excitation spectra that render one a "donor" fluorescent moiety and the other an "acceptor" fluorescent moiety. The two fluorescent moieties are chosen such that the excitation spectrum of the acceptor fluorescent moiety overlaps with the emission spectrum of the excited moiety (the donor fluorescent moiety). The donor moiety is excited by light of appropriate intensity within the excitation spectrum of the donor moiety and emits the absorbed energy as fluorescent light. When the acceptor fluorescent protein moiety is positioned to quench the donor moiety in the excited state, the fluorescence energy is transferred to the acceptor moiety, which can emit a second photon. The emission spectra of the donor and acceptor moieties have minimal overlap so that the two emissions can be distinguished. Thus, when acceptor emits fluorescence at longer wavelength than the donor, then the net steady state effect is that the donor's emission is quenched, and the acceptor now emits when excited at the donor's absorption maximum.

The optical signal can be measured using, for example, a fluorimeter (or the like) to detect fluorescence, including fluorescence polarization, time-resolved fluorescence or FRET. In general, excitation radiation, from an excitation source having a first wavelength, causes the excitation radiation to excite the sample. In response, fluorescent compounds in the sample emit radiation having a wavelength that is different from the excitation wavelength. Methods of performing assays on fluorescent materials are well known in the art and are described, e.g., by Lakowicz (Principles of Fluorescence Spectroscopy, New York, Plenum Press, 1983) and Herman ("Resonance energy transfer microscopy," in: Fluorescence Microscopy of Living Cells in Culture, Part B, Methods in Cell Biology, vol. 30, ed. Taylor & Wang, San Diego, Academic Press, 1989, pp. 219–243). Preferred fluorescence detection techniques are described in further detail below.

In addition, several methods have been described in the literature for using reporter genes to measure gene expression. Nolan et al. describes a technique to analyze β-galactosidase expression in mamralian cells. This technique employs fluorescein-di-β-D-galactopyranoside (FDG) as a substrate for β-galactosidase, which releases fluorescein, a product that can be detected by its fluorescence emission upon hydrolysis (Nolan et al., 1991). Other fluorogenic substrates have been developed, such as 5-dodecanoylamino fluorescein di-β-D-galactopyranoside ($C_{12}$-FDG)(Molecular Probes), which differs from FDG in that it is a lipophilic fluorescein derivative that can easily cross most cell membranes under physiological culture conditions.

The abovementioned β-galactosidase assays may be employed to screen single *E. coli* cells, expressing recombinant β-D-galactosidase isolated, for example from a hyperthermophilic archaeon such as *Sulfolobus solfataricus*. To demonstrate this, cells were cultivated overnight, centrifuged and washed in deionized water and stained with FDG. To increase enzyme activity, the cells were heated to 70° C. for 30 minutes and examined with a fluorescence phase-contrast microscope. The *E. coli* cell suspensions of the β-galactosidase-expressing clone stained with $C_{12}$-FDG showed a very bright fluorescence inside single cells. Other reporter genes may be useful, as substrates are known for β-glucuronidase, alkaline phosphate, chloramphenicol acetyltransferase (CAT) and luciferase.

The present invention also makes it possible to employ mixtures of substrates to detect multiple activities of interest, simultaneously or sequentially. Thus, substrates that fluoresce at different wavelengths and indicate different activities can be employed.

4. Capillary Array

The present invention provides in a preferred embodiment a method for screening an expression library to identify a clone expressing an enzyme having a desired enzyme activity. This method involves, in a preferred embodiment, first generating (e.g., from genomic DNA samples of one or more microorganisms) an expression library, which is preferably multispecific (i.e., derived from more than one species of microorganism). The library comprises a plurality of recombinant clones, which comprise host cells transformed with constructs comprising expression vectors into which have been incorporated nucleic acid sequences derived from the DNA samples. One or more substrates and at least a subset of the clones is then introduced, either individually or together as a mixture, into capillaries (all or a portion thereof) in a capillary array. Interaction (including reaction) of the substrate and a clone expressing an enzyme having the desired enzyme activity produces an optically detectable signal, which can be spatially detected to identify one or more capillaries containing at least one signal-producing clone. The signal-producing clones can then be recovered from the identified capillaries.

In another preferred embodiment, the present invention provides a method for screening an expression library, which is preferably multispecific, to identify a nucleic acid encoding an enzyme having a desired enzyme activity. This method involves, in a preferred embodiment, first generating (e.g., from genomic DNA samples of one or more microorganisms) an expression library comprising a plurality of recombinant clones, wherein the recombinant clones comprise host cells transformed with constructs comprising expression vectors and nucleic acid sequences derived from the DNA samples. One or more substrates and at least a subset of the clones is then introduced, either individually or together as a mixture, into capillaries (all or a portion thereof) in a capillary array. Interaction (including reaction) of the substrate and a clone expressing an enzyme having the desired enzyme activity produces an optically detectable signal, which can be spatially detected to identify one or more capillaries containing at least one clone producing the signal. The signal-producing clones can then be recovered from the identified capillaries. A nucleic acid sequence encoding an enzyme having the desired enzyme activity can then be isolated from a signal-producing clone. This method may further include the step of sequencing the isolated nucleic acid sequence.

In another preferred embodiment, the present invention provides a method of producing a recombinant enzyme having the desired enzyme activity. In this method, a nucleic acid sequence, which encodes an enzyme having a desired enzyme activity, is isolated according to the method described above. This sequence can then be inserted into a suitable expression vector to produce a transformable construct, which can then be used to transform a suitable host cell to produce a recombinant cell. The recombinant enzyme expressed by the recombinant cell can then be recovered.

Existing screening technology usually relies on two-dimensional (2-D) well (e.g., 96-, 384- and 1536-well) plates. The capillary array-based approach of the present invention has numerous advantages over well-based screening techniques, including the elimination of the need for fluid dispensers for dispensing fluids (e.g., reactants) into individual well reservoirs, and the reduced cost per array (e.g., glass. capillaries are reusable). In addition, the waveguide effect of the capillaries in an array constructed with a low refractive index matrix (i.e., the interstitial spaces between the capillary walls in the array are composed of a low refractive index material, such as black glass) can improve optical detectability, since the capillaries act effectively like optical fibers. Moreover, the enzyme discovery throughput using 2-D well plates is typically on the order of about $10^6$ clone-assays per day using a 1536-well plate with conventional automated screening techniques, while that for a capillary-based approach is as high as about $10^9$ clone-assays per day. In the case of the evaporative/wick cycle approach, the present invention also provides the advantages of the possibility of high temperature (up to about 99° C.) assays and the spatial concentration of detectable products in very small volumes (to improve detection sensitivity). Capillary array-based screening techniques also have advantages over FACS-based assays. For example, capillary array-based screening permits standard liquid-phase assays, long-duration assays, and high temperature assays.

The capillary array of the present invention preferably comprises at least about 100 capillaries; more preferably, at least about 1000 capillaries; and, most preferably, at least about 5000 capillaries. In a particularly preferred embodiment, the capillary array comprises about 5000–50000 capillaries. The individual capillaries in the capillary array preferably have an inner diameter (I.D.) of about 10–500 microns; and more preferably, about 50–200 microns.

Preferably, the capillary array has a width (or diameter) of about 0.5–10 cm and a height (or thickness) of about 0.05–10 cm (more preferably, about 0.1–5 cm). The aspect ratio (i.e., ratio of height to width) of the capillary array is preferably at least about 1.

An exemplary capillary array useful in the present invention has a density of at least about 5 capillaries per $mm^2$. The individual capillaries in the array preferably have a cylindrical internal shape, although other geometries and shapes are suitable. The capillaries forming the array may be formed by a variety of methods including, but not limited to, UV excimer laser ablation/drilling/machining, differential glass etching techniques, drawing of hollow glass tubes, silicon lithography, micro-wire EDM, mechanical drilling, electrochemical methods and selective chemical or charged-particle etching techniques.

The capillary array may be formed from a number of suitable materials such as, for example, metal, glass, semiconductors (e.g., silicon), quartz, ceramics, as well as various polymers and plastics including, among others, polyethylene and polypropylene. The internal walls of the capillary array (or portions thereof) may also be coated or functionalized to modify their surface properties. For example, the hydrophilicity/hydrophobicity may be altered to promote or reduce wicking or capillary action, respectively. In addition, the internal walls (or portions thereof) may be silanized or coated with, e.g., Teflon®, to prevent sticking of cells, nucleic acids and other biological materials to the capillary walls. Other coating or functionalizing materials include, for example, ligands such as avidin, streptavidin, antibodies, antigens, and other molecules having specific binding affinity.

The substrate(s) can be contacted with the cells either before or after introduction of the cells into capillaries in the capillary array of the present invention. The substrate and at least a subset of the clones are preferably introduced simultaneously into capillaries in the capillary array by placing open ends of the capillaries (i.e., an open end of the array) in a reservoir containing a mixture of the substrate and clones. By capillary action, the substrate/clone mixture is wicked into the capillaries. The natural wicking which occurs as a result of capillary forces obviates the need for pumping equipment and liquid dispensers. Alternatively, a solution of cells may be wicked into the capillaries before the capillary array is placed in a reservoir containing substrate, where the substrate is then wicked into the capillaries that already contain the cells to be screened for the desired activity.

The substrate solution can then incubated (i.e., maintained in contact) with the cells for a period of time and at an appropriate temperature necessary for cell growth and for the substrate to permeabilize the cell membrane to produce an optically detectable signal. The incubation can be performed, for example, by placing open ends of the capillaries (i.e., an open end of the array) containing the substrate and clones in a reservoir of water or other suitable aqueous solution or liquid (e.g., containing nutrients, etc.). The incubation step can be performed, for example, by transferring the capillary array from a reservoir containing a mixture of clones and substrate to a reservoir containing water. The incubation may be performed under ambient conditions, in which the evaporation of water from the capillaries can transport water, dissolved oxygen, nutrients and additional substrate into the capillaries during incubation. The evaporative flow rate is dependent upon the humidity of the environment. The evaporative flow rate may be reduced by increasing the humidity (e.g., by placing the capillary array in a humidified chamber).

Figure 6:
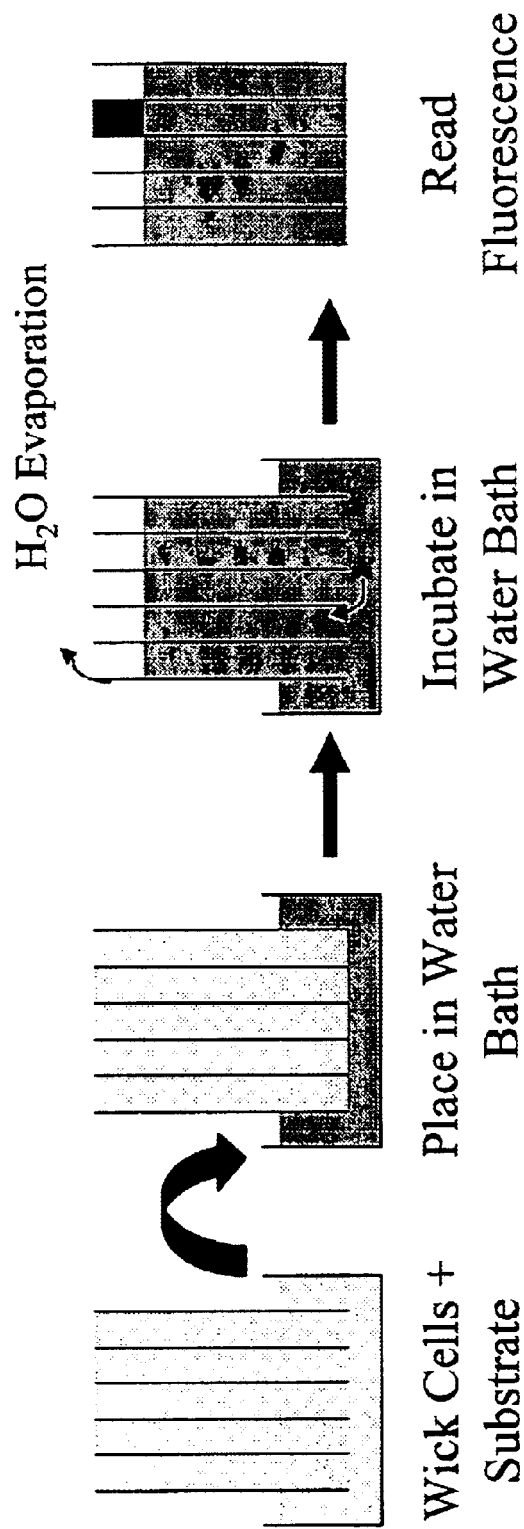
FIG. 6 illustrates one embodiment of the present invention in which a capillary array is placed first into a reservoir containing a mixture of cells and substrate to allow the mixture to be wicked by capillary action into capillaries in the array. The array is transferred to a reservoir containing water (or other aqueous medium) so as to allow the cells to incubate. After incubating for a sufficient time (during which time some of the water evaporates from the capillaries), an optical signal (e.g., fluorescence) indicative of the desired enzyme activity in a given capillary can be spatially detected. This approach is referred to as an evaporative/wick cycle method.

FIG. 6 illustrates one embodiment of the present invention in which a capillary array is placed first into a reservoir containing a mixture of cells and substrate to allow the mixture to be wicked by capillary action into the capillaries in the array. The array is transferred to a reservoir containing water so as to allow the cells to incubate to promote cell growth. After incubating for a sufficient time (during which time some of the water evaporates from the capillaries; the evaporative flow rate depends on the humidity of the environment), an optical signal (e.g., fluorescence) indicative of the desired enzyme activity in a given capillary can be spatially detected. The volume of the water reservoir used for incubation should be sufficiently large compared to the internal volume of the capillary array such that intra-capillary cross-talk (i.e., movement of cells from one capillary in the array to another) is reduced to acceptable levels. Thereby, any components that "leak" out of the capillaries (particularly, cells and fluorescent products) are sufficiently diluted. Alternatively, after introduction of cells and substrate into the capillaries, the ends of the capillaries may be filled with a filter material having selective permeability to permit substrate and water, but not cells, to cross during the incubation period.

Figure 7:
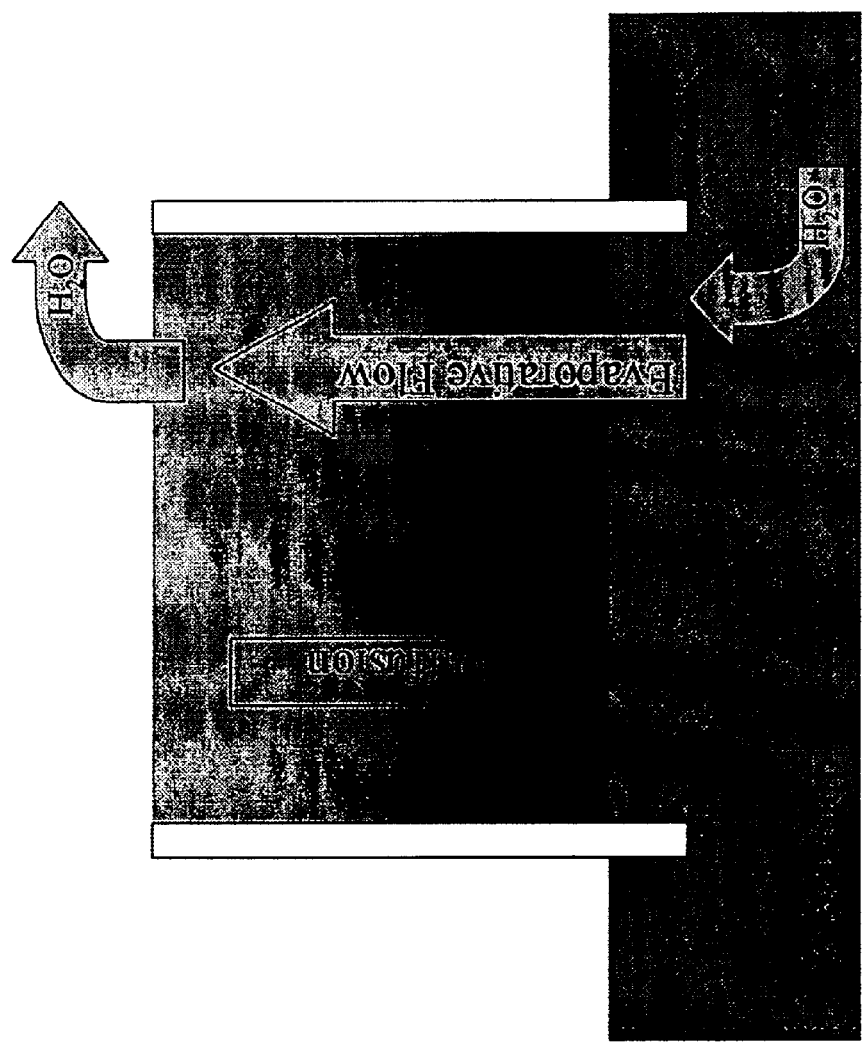
FIG. 7 illustrates the evaporation of water from the capillaries during incubation using the evaporative/wick cycle method shown in FIG. 6.

FIG. 7 illustrates the evaporation of water from the capillaries during incubation. The evaporative/wick cycle can be advantageous in that water, dissolved oxygen, substrate(s) and nutrients can be pulled up into the capillaries during incubation. In addition, end products may be spatially concentrated at or near the top of the capillaries for improved detectability and ease of recovery. Although the capillary array screening is a viable technique without the use of an evaporative/wick cycle or a water incubation reservoir, the duration of the assay (including cell growth) may be limited by evaporation. However the evaporative flow rate can be regulated by adjusting the partial pressure of water vapor (i.e., humidity) at the upper end of the capillary array. The evaporative flow rate is preferably adjusted to approximately equal or exceed the effects of diffusion, density gradients and other "counter-current" effects to minimize "leakage" of the capillary contents. Otherwise, partitioning of capillary contents can occur, leading to insufficient cell growth and/or enzyme-substrate interaction.

Figure 8:
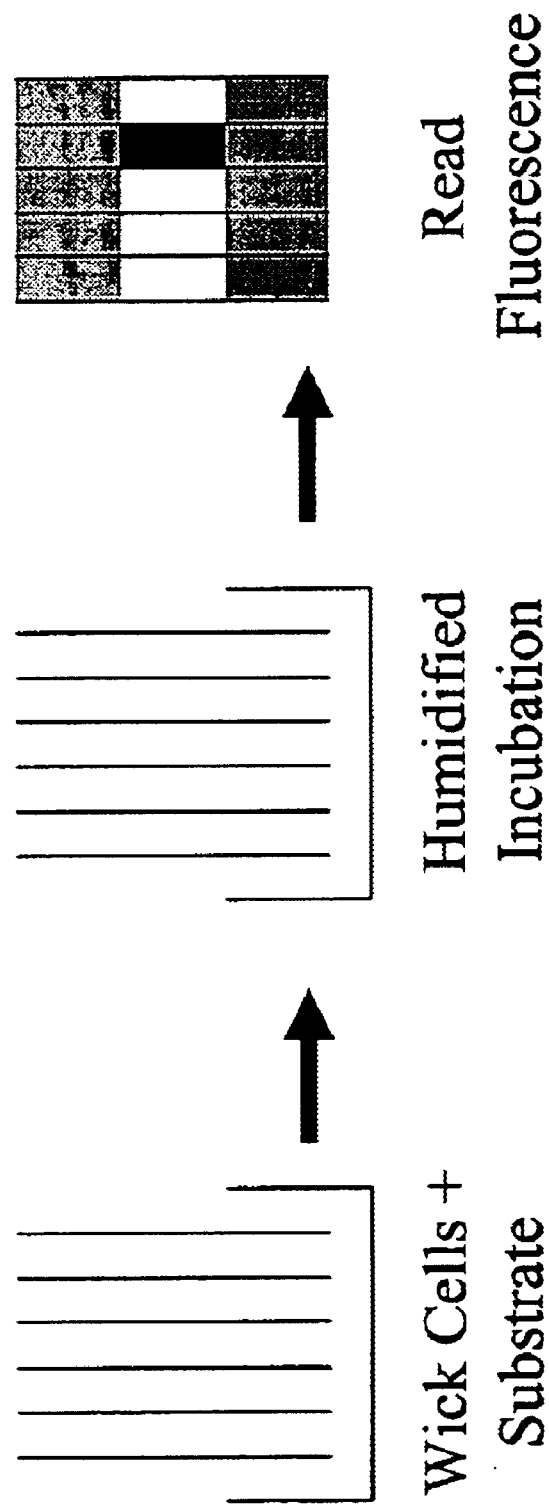
FIG. 8 illustrates another embodiment of the present invention in which a capillary array, after wicking cells and substrate, is incubated in a humidified (or high-humidity) environment.

The evaporation rate may be reduced by placing the capillary array in a high humidity or humidified environment (e.g., a humidified chamber). FIG. 8 illustrates one embodiment of the present invention in which a capillary array, after wicking cells and substrate, is incubated in a humidified environment. The evaporation rate can also be reduced by capping the capillaries with an oil, wax, membrane or the like. Alternatively, a high molecular weight fluid, such as various alcohols, or molecules capable of forming molecular monolayers, bilayers or other thin films (e.g., fatty acids), can be used to reduce evaporation.

The concentration ranges for substrate solutions will vary according to the substrate utilized. Commercially available substrates will generally contain instructions on concentration ranges to be utilized in, for example, cell staining. These ranges may be employed in the determination of an optimal concentration or concentration range to be utilized in the present invention. Such determination is within the purview of the skilled artisan.

The array can be analyzed for identification of capillaries having an optical signal, such as fluorescence, by any detector capable of spatial detection. For example, spatial detection may be performed using a fluorescence excitation beam that directs light through each of the capillaries in the array, and a photodetector (e.g., a photodiode array, charge-coupled device (CCD), or charge-injection device (CID)). The photodetector preferably comprises a CCD, CID or an array of photodiode elements that correspond in positions to the capillaries. Position detection of one of more capillaries having an optical signal is then determined from the optical input from each element. Alternatively, the array may be scanned by a scanning confocal or phase-contrast fluorescence microscope or the like, where the array is, for example, carried on a movable stage for movement in a X-Y plane as the capillaries in the array are successively aligned with the beam to determine the capillary array positions at which an optical signal is detected. A CCD camera or the like can be used in conjunction with the microscope. The detection system is preferably computer-automated for rapid screening and recovery.

Where a chromogenic substrate is used, the change in the absorbance spectrum can be measured using a colorimeter, spectrophotometer or the like. Such calorimetric measurements are usually difficult when dealing with a low-volume liquid because the optical path length is short. However, the capillary approach of the present invention permits small volumes of liquid to have long optical path lengths (i.e., longitudinally along the capillary tube), thereby providing the ability to measure absorbance changes using conventional techniques.

Recovery of putative hits (clones producing an optical signal) can be facilitated by using position feedback from the detection system to automate positioning of a recovery device (e.g., a capillary tube). A "sloppy" recovery can occur if the recovery device has an outer diameter greater than the inner diameter of the capillary from which one or more signal-producing clones is being recovered. A "precise" recovery occurs in a preferred embodiment, in which the recovery device has an outer diameter approximately equal to or less than the inner diameter of the capillary.

After viable or non-viable cells, each containing a different expression clone from the gene library, are screened and positive clones are recovered, the DNA can be isolated from positive clones. This isolated DNA can then be amplified either in vivo or in vitro by utilizing any of the various amplification techniques known in the art. In vivo amplification would include transformation of the clone(s) or subclone(s) of the clones into a viable host, followed by growth of the host. In vitro amplification can be performed using techniques such as the polymerase chain reaction (PCR).

5. Directed Enzyme Mutagenesis

In another embodiment, the present invention provides a method for identifying a mutant or variant enzyme having a desired enzyme activity, further comprising subjecting an isolated enzyme to directed evolution. The directed evolution includes the steps of subjecting the enzyme to non-directed mutagenesis, and screening mutant enzymes produced thereby for a mutant enzyme having the desired enzyme activity.

Clones found to have the activity for which the screen was performed can optionally be subjected to directed mutagenesis to develop new bioactivities with desired properties or to develop modified bioactivities with particularly desired properties that are absent or less-pronounced in the wild-type enzyme, such as stability to heat or organic solvents. Any of the known techniques for directed mutagenesis are applicable to the invention. For example, particularly preferred mutagenesis techniques for use in accordance with the invention include the following:

(i) Error-Prone PCR. The term "error-prone PCR" refers to a process for performing PCR under conditions where the copying fidelity of the DNA polymerase is low, such that a high rate of point mutations is obtained along the entire length of the PCR product. Leung, D. W., et al., Technique, 1:11–15 (1989) and Caldwell, R. C. & Joyce G. F., PCR Methods Applic., 2:28–33 (1992).

(ii) Oligonucleotide Directed Mutagenesis. The term "oligonucleotide directed mutagenesis" refers to a process which allows for the generation of site-specific mutations in any cloned DNA segment of interest. Reidhaar-Olson, J. F. & Sauer, R. T., et al., Science, 241:53–57 (1988).

(iii) Sexual PCR Mutagenesis. The term "sexual PCR mutagenesis" (also known as "DNA shuffling") refers to forced homologous recombination between DNA molecules of different but highly related DNA sequence in vitro, caused by random fragmentation of the DNA molecule based on sequence homology, followed by fixation of the crossover by primer extension in a PCR reaction. Stemmer, W. P., PNAS USA, 91:10747–10751 (1994).

(iv) In Vivo Mutagenesis. The term "in vivo mutagenesis" refers to a process of generating random mutations in any cloned DNA of interest which involves the propagation of the DNA in a strain of E. coli that carries mutations in one or more of the DNA repair pathways. These "mutator" strains have a higher random mutation rate than that of a wild-type parent. Propagating the DNA in one of these strains will eventually generate random mutations within the DNA.

(v) Cassette Mutagenesis. The term "cassette mutagenesis" refers to any process for replacing a small region of a double stranded DNA molecule with a synthetic oligonucleotide "cassette" that differs from the native sequence. The oligonucleotide often contains completely and/or partially randomized native sequence.

(vi) Recursive Ensemble Mutagenesis. The term "recursive ensemble mutagenesis" refers to an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Arkin, A. P. and Youvan, D. C., PNAS USA, 89:7811–7815 (1992).

(vii) Exponential Ensemble Mutagenesis. The term "exponential ensemble mutagenesis" refers to a process for generating combinatorial libraries with a high percentage of unique and functional mutants, wherein small groups of residues are randomized in parallel to identify, at each altered position, amino acids which lead to functional proteins, Delegrave, S. and Youvan, D. C., Biotechnology Research, 11:1548–1552 (1993); and random and site-directed mutagenesis, Arnold, F. H., Current Opinion in Biotechnology, 4:450–455 (1993).

All of the references mentioned above in connection with directed mutagenesis are hereby incorporated by reference in their entirety.

DNA can be mutagenized, or "evolved", utilizing any one or more of these techniques, and rescreened to identify more desirable clones. Internal control reference genes which either express fluorescing molecules, such as those encoding green fluorescent protein, or encode proteins that can turn-over fluorescing molecules, such as beta-galactosidase, can be utilized. These internal controls should optimally fluoresce at a wavelength which is different from the wavelength at which the molecule used to detect the evolved molecule(s) emits. DNA is evolved, recloned in a vector that co-expresses these proteins or molecules, transformed into an appropriate host organism, and rescreened to identify more desirable clones.

Without further elaboration, it is believed that one skilled in the art can, using the preceding description, utilize the present invention to its fullest extent. The following examples are illustrative only and are not intended to limit the scope of the present invention, which is defined by the claims appended hereto.

EXAMPLES

Example 1

DNA Isolation and Library Construction

The following outlines one procedure that may be used to generate a library from genomic DNA samples isolated from an environmental sample (see FIG. 1).

DNA isolation. DNA is isolated using the IsoQuick Procedure as per manufacturer's instructions (Orca Research Inc., Bothell, Wash.). The isolated DNA can optionally be normalized according to Example 2 below. Upon isolation, the DNA is sheared by pushing and pulling the NA through a 25-gauge double-hub needle and a 1-cc syringe about 500 times. A small amount is run on a 0.8% agarose gel to make sure the majority of the DNA is in the desired size range (about 3–6 kb).

Blunt-ending DNA. The DNA is blunt-ended by mixing 45 μl of 10X Mung Bean Buffer, 2.0 pl Mung Bean Nuclease (150 u/μl) and water to a final volume of 405 μl. The mixture is incubated at 37° C. for 15 minutes. The mixture is phenol/chloroform extracted, followed by an additional chloroform extraction. One ml of ice cold ethanol is added to the final extract to precipitate the DNA. The DNA is precipitated for 10 minutes on ice. The DNA is removed by centrifugation in a microcentrifuge for 30 minutes. The pellet is washed with 1 ml of 70% ethanol and repelleted in the microcentriluge. Following centrifigation, the DNA is dried and gently resuspended in 26 μl of TE buffer.

Methylation of DNA. The DNA is methylated by mixing 4 pl of 10X EcoR I Methylase Buffer, 0.5 μl SAM (32 mM), 5.0 μl EcoR I Methylase (40 u/μl) and incubating at 37° C., 1 hour. In order to insure blunt ends, the following can be added to the methylation reaction: 5.0 μl of 100 mm $MgCl_2$, 8.0 μl of dNTP mix (2.5 mM of each dGTP, dATP, dTTP, dCTP), 4.0 μl of Klenow (5 u/μl). The mixture is then incubated at 12° C. for 30 minutes.

After incubating for 30 minutes add 450 μl 1X STE is added. The mixture is phenol/chloroform extracted once followed by an additional chloroform extraction. One ml of ice cold ethanol is added to the final extract to precipitate the DNA. The DNA is precipitated for 10 minutes on ice. The DNA is removed by centrifugation in a microcentrifuge for 30 minutes. The pellet is washed with 1 ml of 70% ethanol, repelleted in the microcentrifuge and allowed to dry for 10 minutes.

Ligation. The DNA is ligated by gently resuspending the DNA in 8 μl EcoR I adaptors (from Stratagene's cDNA Synthesis Kit), 1.0 μl of 10X Ligation Buffer, 1.0 μl of 10 mM rATP, 1.0 μl of T4 DNA Ligase (4Wu/μl) and incubating at 4° C. for 2 days. The ligation reaction is terminated by heating for 30 minutes at 70° C.

Phosphorylation of adaptors. The adaptor ends are phosphorylated by mixing the ligation reaction with 1.0 μl of 10X Ligation Buffer, 2.0 μl of 10 mM rATP, 6.0 μl of $H_2O$, 1.0 μl of polynucleotide kinase (PNK), and incubating at 37° C. for 30 minutes. After incubating for 30 minutes, 31 μl of $H_2O$ and 5 ml of 10X STE are added to the reaction and the sample is size fractionated on a Sephacryl S-500 spin column. The pooled fractions (1–3) are phenol/chloroform extracted once, followed by an additional chloroform extraction. The DNA is precipitated by the addition of ice cold ethanol on ice for 10 minutes. The precipitate is pelleted by centrifugation in a microcentrifuge at high speed for 30 minutes. The resulting pellet is washed with 1 ml 70% ethanol, repelleted by centrifugation and allowed to dry for 10 minutes. The sample is resuspended in 10.5 μl TE buffer. The sample isnot plated, but is ligated directly to lambda arms as described above, except 2.5 μl of DNA and no water are used.

Sucrose Gradient (2.2 ml) Size Fractionation. Ligation is stopped by heating the sample to 65° C. for 10 minutes. The sample is gently loaded on a 2.2 ml sucrose gradient and centrifuged in a mini-ultracentrifuge 45 k rpm at 20° C. for 4 hours (no brake). Fractions are collected by puncturing the bottom of the gradient tube with a 20-gauge needle and allowing the sucrose to flow through the needle. The first 20 drops are collected in a Falcon 2059 tube, and then ten 1-drop fractions (labeled 1–10) are collected. Each drop is about 60 μl in volume. Five l of each fraction are run on a 0.8% agarose gel to check the size. Fractions 1–4 (about 10–1.5 kb) are pooled and, in a separate tube, fractions 5–7 (about 5–0.5 kb) are pooled. One ml of ice cold ethanol is added to precipitate the DNA and then placed on ice for 10 minutes. The precipitate is pelleted by centrifugation in a microcentrifnge at high speed for 30 minutes. The pellets are washed by resuspending them in 1 ml of 70% ethanol and repelleting them by centrifugation in a microcentrifuge at high speed for 10 minutes, and then dried. Each pellet is then resuspended in 10 μl of TE buffer.

Test Ligation to Lambda Arms. The assay is plated by spotting 0.5 μl of the sample on agarose containing ethidiurm bromide along with standards (DNA samples of known concentration) to get an approximate concentration. The samples are then viewed using UV light and the estimated concentration is compared to the standards. Fraction 1–4= >1.0 μg/μl. Fraction 5–7=500 ng/μl.

The following ligation reactions (5 μl reactions) are prepared and incubated at 4° C. overnight, as shown in Table 1 below:

TABLE 1

| Sample | H$_2$O | 10× Ligase Buffer | 10 mM rATP | Lambda arms (ZAP) | Insert DNA | T4 DNA Ligase (4 Wu/(1) |
|---|---|---|---|---|---|---|
| Fraction 1–4 | 0.5 μl | 0.5 μl | 0.5 μl | 1.0 μl | 2.0 μl | 0.5 μl |
| Fraction 5–7 | 0.5 μl | 0.5 μl | 0.5 μl | 1.0 μl | 2.0 μl | 0.5 μl |

Test Package and Plate. The ligation reactions are packaged following manufacturer's protocol. Packaging reactions are stopped with 500 μl SM buffer and pooled with packaging that came from the same ligation. One μl of each pooled reaction is titered on an appropriate host (OD$_{600}$= 1.0)[XLI-Blue MRF]. 200 μl host (in mM MgSO$_4$) are added to Falcon 2059 tubes, inoculated with 1 μl packaged phage and incubated at 37° C. for 15 minutes. About 3 ml of 48° C. top agar [50 ml stock containing 150 μl IPTG (0.5M) and 300 μl X-GAL (350 mg/ml)] are added and plate on 100 mm plates. The plates are incubated overnight at 37° C.

Amplification of Libraries (5.0×10$^5$ recombinants from each library). About 3.0 ml host cells (OD$_{600}$=1.0) are added to two 50 ml conical tubes, inoculated with 2.5×10$^5$ pfu of phage per conical tube, and then incubate at 37° C. for 20 minutes. Top agar is added to each tube to a final volume of 45 ml. Each tube is plated across five 150 mm plates. The plates are incubated at 37° C. for 6–8 hours or until plaques are about pin-head in size. The plates are overlaid with 8–10 ml SM Buffer and placed at 4° C. overnight (with gentle rocking if possible).

Harvest Phage. The phage suspension is recovered by pouring the SM buffer off each plate into a 50-ml conical tube. About 3 ml of chloroform are added, shaken vigorously and incubated at room temperature for 15 minutes. The tubes are centrifuged at 2 k rpm for 10 minutes to remove cell 20 debris. The supernatant is-poured into a sterile flask, 500 μl chloroform are added and stored at 4° C.

Titer Amplified Library. Serial dilutions of the harvested phage are made (for example, 10$^{-5}$=1 μl amplified phage in 1 ml SM Buffer; 10$^{-6}$=1 μl of the 10$^{-3}$ dilution in 1 ml SM Buffer), and 200 μl host (in 10 mM MgSO$_4$) are added to two tubes. One tube is inoculated with 10 μl 10$^{-6}$ dilution (10$^{-5}$). The other tube is inoculated with 1 μl 10$^{-6}$ dilution (10$^{-6}$), and incubated at 37° C. for 15 minutes.

About 3 ml of 48° C. top agar [50 ml stock containing 150 μl IPTG (0.5M) and 375 μl X-GAL (350 mg/ml)] are added to each tube and plated on 100 mm plates. The plates are incubated overnight at 37° C.

The ZAP II library is excised to create the pBLUE-SCRIPT library according to manufacturers protocols (Stratagene).

The DNA library can be transformed into host cells (e.g., *E. coli*) to generate an expression library of clones.

Example 2

Normalization

Prior to library generation purified DNA can be normalized. DNA is first fractionated according to the following protocol. A sample composed of genomic DNA is purified on a cesium-chloride gradient. The cesium chloride (Rf= 1.3980) solution is filtered through a 0.2 μm filter and 15 ml is loaded into a 35 ml OptiSeal tube (Beckmnan). The DNA is added and thoroughly mixed. Ten micrograms of bis-benzimide (Sigma; Hoechst 33258) is added and mixed thoroughly. The tube is then filled with the filtered cesium chloride solution and spun in a VTi50rotor in a Beckmran L8-70 Ultracentrifuge at 33 k rpm for 72 hours. Following centriftigation, a syringe pump and fractionator (Brandel Model 186) are used to drive the gradient through an ISCO UA-5 UV absorbance detector set to 280 nm. Peaks representing the DNA from the organisms present in an environmental sample are obtained. Eubacterial sequences can be detected by PCR amplification of DNA encoding rRNA from a 10-fold dilution of the *E. coli* peak using the following primers to amplify:

Forward primer: 5'-AGAGTTTGATCCTGGCTCAG-3' (SEQ ID NO:1)

Reverse primer: 5'-GGTTACCTTGTTACGACTT-3' (SEQ ID NO:2)

Recovered DNA is sheared or enzymatically digested to 3–6 kb fragments. Lone-linker primers are ligated and the DNA is size-selected. Size-selected DNA is amplified by PCR, if necessary.

Normalization is then accomplished by resuspending the double-stranded DNA sample in hybridization buffer (0.12 M NaH$_2$PO$_4$, pH 6.8/0.82 M NaCl/l mM EDTA/0.1% SDS). The sample is overlaid with mineral oil and denatured by boiling for 10 minutes. The sample is incubated at 68° C. for 12–36 hours. Double-stranded DNA is separated from single-stranded DNA according to standard protocols (Sambrook, 1989) on hydroxyapatite at 60° C. The single-stranded DNA fraction is desalted and amplified by PCR. The process is repeated for several more rounds (up to 5 or more).

Example 3

Optical Detection of Enzyme Activity in Individual Capillaries Using an Evaporative-Wick Cycle Approach.

Cell growth and enzyme activity were verified by wicking, through capillary action, a series of cell dilutions (clone # 604-1 α-gal positive) mixed with substrate (100 μM Umbα-gal) into individual capillary tubes. Each of the capillary tubes had a 100 μm inner diameter (I.D.) and 32 mm length (1 μl volume). Specifically, the wicking of the cell/substrate mixture was accomplished by placing an open end of the capillary tube into a reservoir containing a mixture of the positive cell clones and the Umb substrate. The same mixture was also plated out to confirm starting cell densities (CFU/tube@t=0). The tubes were then incubated overnight at 37° C. with their open ends submerged in a water bath.

A photomicrograph of various capillary tubes was obtained using an Eagle Eyes® (Stratagene; San Diego, Cailf.) modified with a different emission/blocking filter (Schott GG435). Tubes A through F (see dilutions in Table 2 below) all showed enzyme activity, as evidenced by detection of substrate fluorescence. Tube G was a negative control (cells with no substrate). The contents of each tube were then plated (by Flash) and again colonies were counted. The results (see Table 2 below) show that the number of viable cells per capillary tube after incubation was approximately 3000 (CFU/tube @ t=0).

TABLE 2

| Tube | Dilution | Approximate CFU/Tube @ t = 0 | Approximate CFU/Tube @ t = 0/N |
|---|---|---|---|
| A | $10^{-1}$ | 100,000 | 3000 |
| B | $10^{-2}$ | 10,000 | 3000 |
| C | $10^{-3}$ | 1,000 | 3000 |
| D | $10^{-4}$ | 100 | 3000 |
| E | $10^{-5}$ | 10 | 3000 |
| F | $10^{-6}$ | 1 | 500 |
| G | Stock (no substrate) | 1,000,000 | 3000 |

Example 4

Schott Capillary Array-Based Optical Detection of Enzyme Activity Using an Evaporative-Wick Cycle Approach Image-based optical detection of substrate fluorescence was verified in a capillary array (Schott Fiber Optics; Southibridge, Mass.) containing 5551 pores (200 μm I.D.×2 mm length; 60 nl volume) by spotting a series of four dilutions of Umb (100 μM, 10 μM, 1 μM and 0.1 μM) onto the array. As can be seen in FIG. 12, due to cell auto-fluorescence, the detectable threshold concentration under these conditions is approximately 10 μM.

Detection of cell growth and enzyme activity on a capillary array-were also confirmed. Positive and negative clones at a variety of cell densities were mixed with substrate (50 μM Umb cc-gal) and-manually spotted onto a Schott capillary array. The array was then floated on a water bath and incubated at 37° C. In most cases, visual inspection showed that the cells had grown within the array, although the cells appeared morphologically different.

However, some difficulties were observed using the Umb substrate due to its high excitation energy requirements. Cell auto-fluorescence limited detectability, and dust, which is also fluorescent with UV excitation, was a source of some false positive results. The fluorophore resorufm, which requires lower excitation energies, was investigated as an alternative to Umb. The resorufin β-D-glucuronide substrate was mixed with the same clone # 604-1 cells used above (most E. coli strains have an endogenous glucuronidase). The resorufin was brightly red fluorescent with very little background fluorescence due to cells or contamination.

Example 5

CHI Capillary Array-Based Optical Detection of Enzyme Activity Using an Evaporative-Wick Cycle Approach Detection of enzyme activity within another capillary array was shown by spotting solutions of cells and substrate onto an array obtained from Collimated Holes Inc. (CHI; Campbell, Cailf.). The CHI capillary array contained approximately 34,000 pores, each having 50 μm I.D. and 5 mm length (volume=10 nl; diameter=13 mm). A liquid culture of a positive β-gal clone (clone # 535GL2) was diluted to make solutions containing approximately 1, 10, and 100 cells per capillary. The three solutions, which also contained 50 μM (final) β-gal Resorufin substrate, were spotted onto the CHI array. The 100 cells/capillary solution was spotted onto the upper-left quadrant of the array; the 10 cells/capillary solution was spotted onto the upper-right quadrant; and the 1 cell/capillary solution was spotted onto the lower-left quadrant. A fourth solution, containing approximately 100 cells/pore of a negative β-gal clone (clone # 632), was similarly prepared and spotted onto the lower-right quadrant of the array. The array was floated on a water bath and incubated at 37° C. Fluorescence images were taken after 3 hours 24 hours of incubation using a 550 nm excitation interference filter and a 590 run long-pass glass filter. All three spots on the CHI array containing the solution of positive clones had a strong fluorescence signal indicative of β-gal activity, whereas the spot containing the negative clones (lower-right quadrant) showed none. The enzymatic product did not significantly diffuse into the water bath or the surrounding capillaries in the capillary array. This Example demonstrates that enzyme activity from a positive genomic clone can be detected in a capillary array.

Example 6

Humidified Chamber Approach

Figure 9:
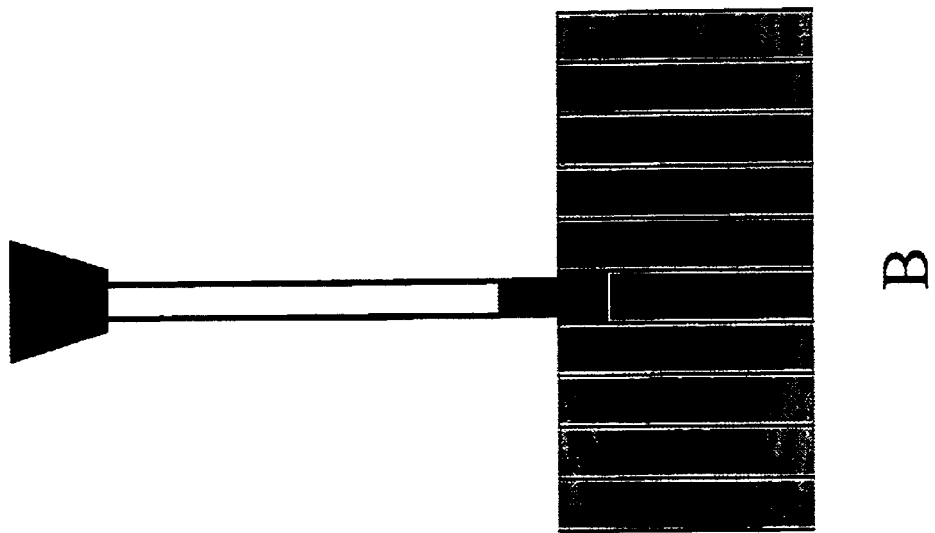
FIG. 9 illustrates the recovery of clones from a given capillary having an optical signal.
Figure 9:
Figure 10:
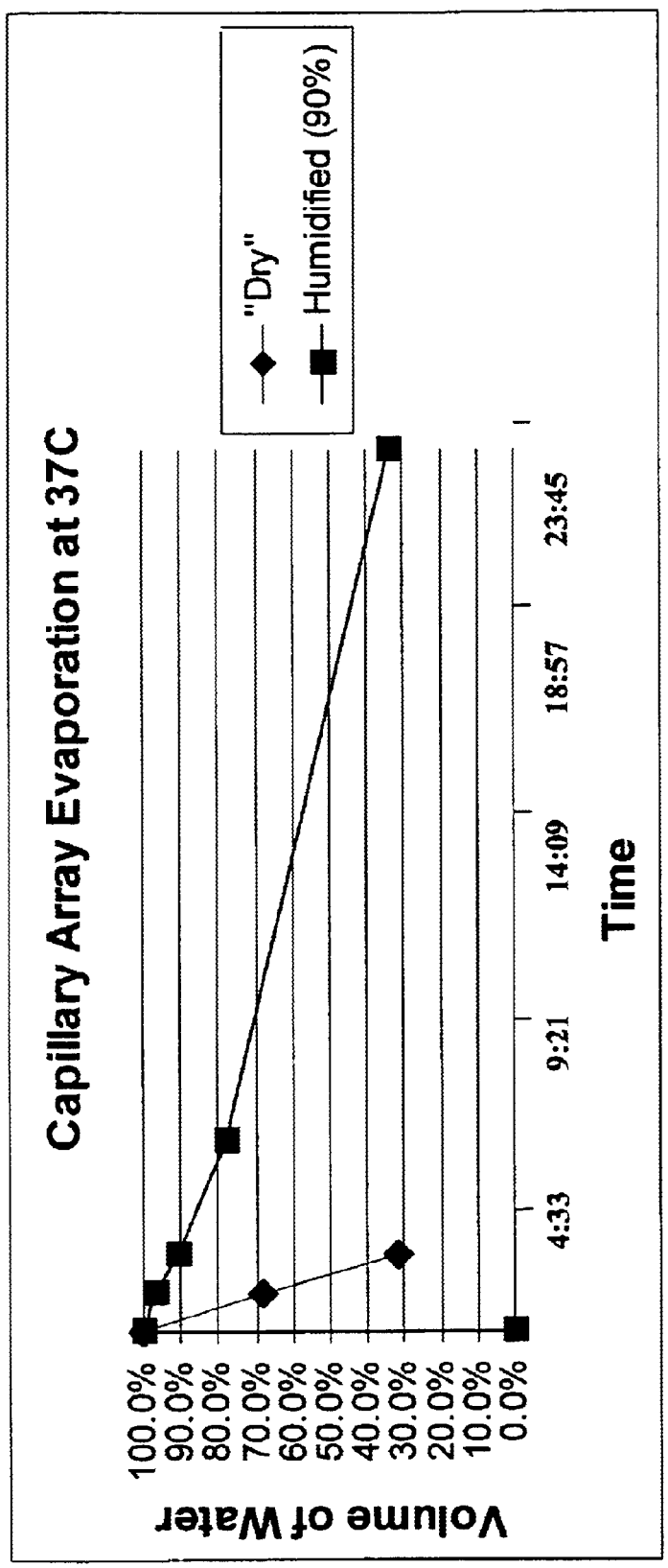
FIG. 10 is a graph comparing the evaporation rate over an approximately 24-hour period from a capillary array in a humidified chamber with a relative humidity (RH)=90% versus that in an unhumidified chamber (RH low).

Incubation of capillary arrays in a humidified chamber was tested as an alternative to the evaporative-wick cycle method for maintaining hydration (see Examples 3–5 above). A CHI array that was originally filled with water was weighed periodically during a 37° C. incubation cycle in both a humidified (RH=90%) and unhumidified (RH low) chamber. Weight loss was used to indicate the amount of evaporation from the array. The results in FIG. 9 show that after 19 hours almost half of the contents of the humidified array are retained. These conditions should be adequate for cell growth and detection of enzyme activity. A similar experiment at even higher humidity (RH≈95%) was conducted. Condensation prevented accurate measurement of evaporation, but visual inspection revealed very little evaporative loss over a period of several days.

Cited Literature

Adams, M. W. W. and Kelly, R. M, *Chemical and Engineering News*, 1995, Dec. 18.

Amann, R. Ludwig, W. and Schleifer, K.-H., *Microbiological Reviews*, 1995, 59, 143.

Barnes, S. M., Fundyga, R. E., Jeffries, M. W. and Pace, N. R., *Proc. Natl. Acad. Sci. USA*, 1994, 91, 1609.

Bateson, M. M., Wiegel, J. and Ward, D. M., *System. Appl. Microbiol.*, 1989, 12, 1–7.

Davey, H. M. and Kell, D. B., *Microbiological Reviews*, 1996, 60, 4, 641–696.

*Enzyme Nomenclature*, Academic Press: NY, 1992.

Faber, Biotransformation in Organic Chemistry, 2nd edition, Springer Verlag, 1995.

Faber, Tonkovich and Gerber, U.S. Dept. of Energy Study, 1995.

Giovannoni, S. J., Britschgi, T. B., Mover, C. L. and Field, K. G., *Nature*, 1990 345, 60–63.

Plovins A., Alvarez A. M., Ibanez M., Molina M. and Nombela C., *Appl. Environ. Microbiol.*, 1994, 60, 463–84641.

Tonkovich, A. L. and Gerber, M. A., U.S. Dept. of Energy, Office of Industrial Technology, Biological and Chemical Technologies Research Program under contract DE-AC06-76RLO 0 1830.

Torvsik, V. Goksoyr, J. and Daae, F. L., *Appl. and Environm. Microbiol.*, 1990, 56, 782–787.

Wrotnowski, *Genetic Engineering News*, 1997, Feb. 1.

The disclosure of each of the cited references is incorporated herein by reference in its entirety.

It will be apparent to those skilled in the art that various modifications and substitutions can be made to the compounds and processes of this invention. Thus, the present invention covers such that come within the scope of the appended claims and their equivalents.

What is claimed is:

1. A method for identifying a clone expressing an enzyme, the method comprising:
  (a) generating an expression library comprising a plurality of recombinant clones comprising nucleic acid sequences derived from genomic DNA samples of at least one microorganism;
  (b) introducing a mixture of a substrate selected for being specific for an enzyme selected from lipases, esterases, proteases, peptidases, reductases, oxidoreductases, lyases, ligases, isomerases, polymerases, synthases, synthetases, glycosidases, transferases, phosphatases, kinases, mono-and dioxygenases, peroxidases, hydrolases, hydratases, nitrilases, transaminases, amidases and acylases and clones from the library into capillaries in a capillary array;
  (c) incubating the clones with the substrate in the capillary-array in a reservoir containing water for a period of time to allow water to evaporate in the capillaries sufficient for at least one of the clones to express an enzyme that interacts with the substrate to produce an optically detectable signal;
  (d) spatially detecting the signal to identify at least one capillary containing at least one signal-producing clone; and
  (e) recovering the signal-producing clone from the identified capillary, thereby identifying a clone expressing an enzyme having the desired enzymatic activity.

2. The method of claim 1, wherein the expression library is generated from genomic DNA samples of at least one microorganism and the recombinant clones comprise host cells transformed with constructs comprising the nucleic acid sequences derived from the DNA samples.

3. The method of claim 2, wherein the microorganisms comprise prokaryotic cells.

4. The method of claim 2, wherein the microorganisms are a plurality of microorganisms.

5. The method of claim 2, wherein the microorganisms are derived from an environmental sample.

6. The method of claim 2, wherein the microorganisms are selected from the group consisting of terrestrial microorganisms, marine microorganisms and airborne microorganisms.

7. The method of claim 6, wherein the microorganisms comprise extremophiles.

8. The method of claim 7, wherein the extremophiles are thermophiles.

9. The method of claim 7, wherein the extremophiles are selected from the group consisting of hyperthermophiles, psychrophiles, halophiles, psychrotrophs, alkalophiles and acidophiles.

10. The method of claim 2, wherein the host cells are selected from the group consisting of bacterial cells, fungal cells, plant cells, insect cells and animal cells.

11. The method of claim 2, wherein the host cells are prokaryotic cells.

12. The method of claim 11, wherein the prokaryotic cells are bacterial cells.

13. The method of claim 12, wherein the bacterial cells are *E. coli*.

14. The method of claim 1, wherein the substrate is a chromogenic substrate.

15. The method of claim 1, wherein the substrate is a fluorogenic substrate.

16. The method of claim 15, wherein the signal is optical fluorescence.

17. The method of claim 15, wherein the fluorogenic substrate comprises umbelliferone.

18. The method of claim 15, wherein the fluorogenic substrate comprises resorufin.

19. The method of claim 15, wherein the fluorogenic substrate comprises fluorescein.

20. The method of claim 15, wherein the fluorogenic substrate comprises rhodamine.

21. The method of claim 1, wherein the detection is provided by a detector comprising a CCD, CID or photodiode array.

22. The method of claim 1, wherein the capillary array comprises at least about 100 capillaries.

23. The method of claim 1, wherein the capillary array comprises at least about 1000 capillaries.

24. The method of claim 1, wherein the capillary array comprises at least about 5000 capillaries.

25. The method of claim 1, wherein the substrate liquid and the clones are introduced simultaneously as a cell/substrate liquid mixture into capillaries in the capillary array.

26. The method of claim 1, further comprising biopanning prior to (b).

27. The method of claim 2, further comprising normalizing the genomic DNA prior to generating the expression library.

28. The method of claim 1, further comprising isolating at least one enzyme from the recovered clones.

29. A method for producing a recombinant enzyme having a desired enzyme activity, comprising:
  (a) generating an expression library comprising a plurality of recombinant clones comprising nucleic acid sequences isolated from genomic DNA samples of at least one microorganism;
  (b) introducing a mixture of a cell permeabilizing substrate specific for an enzyme selected from lipases, esterases, proteases, peptidases, reductases, oxidoreductases, lyases, ligases, isomerases, polymerases, synthases, synthetases, glycosidases, transferases, phosphatases, kinases, mono-and dioxygenases, peroxidases, hydrolases, hydratases, nitrilases, transaminases, amidases and acylases and recombinant clones from the library into capillaries in a capillary array;
  (c) incubating the substrate and the clones in the capillaries to allow specific intracellular interaction of the substrate and a recombinant clone expressing the enzyme having the desired enzyme activity to produce an optically detectable signal;
  (c) spatially detecting the signal to identify at least one capillary containing at least one signal-producing recombinant clone;
  (d) recovering the signal-producing recombinant clone from identified capillaries;
  (e) isolating a nucleic acid sequence from a signal-producing recombinant clone, wherein the nucleic acid sequence encodes an enzyme having the desired specific enzyme activity;
  (f) inserting the nucleic acid sequence isolated in (e) into a suitable expression vector to produce a transformable construct;
  (g) transforming a suitable host cell with a sequence comprising the transformable construct produced in (f) to produce a recombinant cell; and
  (h) recovering from the recombinant cell produced in (g) a recombinant enzyme having the desired enzyme activity expressed by the recombinant cell.

* * * * *